United States Patent [19]

Bruneau et al.

[11] Patent Number: 5,367,079
[45] Date of Patent: Nov. 22, 1994

[54] CYCLOALKANE DERIVATIVES

[75] Inventors: Pierre A. R. Bruneau, Ludes; Christine M. P. Lambert-van der Brempt, Echenay, both of France

[73] Assignees: Zeneca Limited, London, England; Zeneca-Pharma, S.A., Cergy Cedex, France

[21] Appl. No.: 51,395

[22] Filed: Apr. 23, 1993

[30] Foreign Application Priority Data

Apr. 23, 1992 [EP] European Pat. Off. ........ 92401159.6

[51] Int. Cl.$^5$ .................. C07D 215/48; C07D 215/38; C07D 215/20; C07D 215/18
[52] U.S. Cl. ..................... 546/157; 546/153; 544/333; 544/300
[58] Field of Search ................ 546/157, 153; 514/312; 544/333, 300

[56] References Cited

U.S. PATENT DOCUMENTS

| | | | |
|---|---|---|---|
| 4,567,184 | 1/1986 | Musser et al. | 514/277 |
| 4,625,034 | 11/1986 | Neiss et al. | 546/152 |
| 4,631,287 | 12/1986 | Chakraborty | 514/307 |
| 4,661,596 | 4/1987 | Kreft, III et al. | 546/152 |
| 4,681,940 | 7/1987 | Musser et al. | 546/174 |
| 4,725,619 | 2/1988 | Chakaborty et al. | 514/442 |
| 4,728,668 | 3/1988 | Chakraborty et al. | 514/464 |
| 4,794,188 | 12/1988 | Musser et al. | 546/152 |
| 4,839,369 | 6/1989 | Youssefyeh et al. | 514/314 |

(List continued on next page.)

FOREIGN PATENT DOCUMENTS

| | | |
|---|---|---|
| 0110405 | 6/1984 | European Pat. Off. . |
| 0181568 | 5/1986 | European Pat. Off. . |
| 0271287 | 6/1986 | European Pat. Off. . |
| 271287 | 6/1986 | European Pat. Off. . |
| 0190722 | 8/1986 | European Pat. Off. . |
| 0200101 | 12/1986 | European Pat. Off. . |
| 0462820 | 12/1991 | European Pat. Off. . |

OTHER PUBLICATIONS

John H. Musser & Utpal R. Chakraborty; Substituted Arylnethyl Phenyl Ethers; Journal of Medicinal Chemistry, vol. 30, No. 1; 1987; pp. 96–104.

Primary Examiner—C. Warren Ivy
Assistant Examiner—D. Margaret M. Mach
Attorney, Agent, or Firm—Cushman, Darby & Cushman

[57] ABSTRACT

The invention concerns cycloalkane derivatives of the formula I

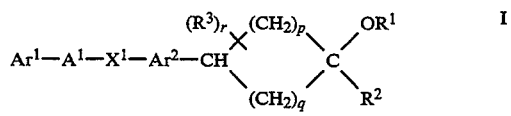

wherein
$Ar^1$ is phenyl, naphthyl or a 10-membered bicyclic heterocyclic moiety which may optionally bear up to four substituents;
$A^1$ is a direct link to $X^1$ or is (1–3C)alkylene;
$X^1$ is oxy, thio, sulphinyl or sulphonyl;
$Ar^2$ is phenylene, pyridylene, pyrimidinylene, thiophenediyl, furandiyl, thiazolediyl or oxazolediyl which may optionally bear one or two substituents;
p is 1 to 4;
q is 0 to 2;
$R^1$ is hydrogen, (1–4C)alkyl, (2–4C)alkenyl or (3–4C)alkynyl;
$R^2$ is hydrogen, hydroxy, (1–4C)alkyl, (1–4C)alkoxy, (2–4C)alkenyloxy or (3–4C)alkynyloxy;
or the $OR^1$ and $R^2$ groups together form a (1–4C)alkylenedioxy, oxo, thioxo, imino, hydroxyimino or (1–4C)alkoxyimino group;
r is 0 to 3; and
$R^3$ is halogeno, trifluoromethyl or (1–4C)alkyl;
or a pharmaceutically-acceptable salt thereof;

processes for their manufacture; pharmaceutical compositions containing them and their use as 5-lipoxygenase inhibitors.

8 Claims, No Drawings

U.S. PATENT DOCUMENTS

| | | | |
|---|---|---|---|
| 4,859,679 | 8/1989 | Santini | 514/273 |
| 4,868,193 | 9/1989 | Lee | 514/314 |
| 4,874,769 | 10/1989 | Youssefyeh et al. | 514/314 |
| 4,876,346 | 10/1989 | Musser et al. | 546/172 |
| 5,006,534 | 4/1991 | Mohrs et al. | 514/311 |
| 5,098,930 | 3/1992 | Edwards et al. | 514/459 |
| 5,098,932 | 3/1992 | Hamon | 549/449 |
| 5,105,020 | 4/1992 | Girodeau | 568/633 |
| 5,134,148 | 7/1992 | Crawley et al. | 514/312 |
| 5,137,913 | 8/1992 | Bird et al. | 514/467 |
| 5,179,115 | 1/1993 | Bruneau et al. | 514/387 |
| 5,196,419 | 3/1993 | Crawley et al. | 514/241 |
| 5,208,259 | 5/1993 | Bird et al. | 514/460 |
| 5,214,070 | 5/1993 | Bird et al. | 514/708 |
| 5,217,969 | 6/1993 | Bruneau et al. | 514/230.5 |
| 5,217,977 | 6/1993 | Crawley | 514/311 |
| 5,217,978 | 6/1993 | Bird | 514/312 |
| 5,219,881 | 6/1993 | Hamon | 514/452 |
| 5,221,677 | 6/1993 | Crawley et al. | 514/309 |
| 5,225,438 | 7/1993 | Dowell et al. | 514/459 |
| 5,234,950 | 8/1993 | Edwards et al. | 514/473 |
| 5,236,919 | 8/1993 | Crawley et al. | 514/349 |
| 5,236,948 | 8/1993 | Waterson | 514/459 |
| 5,294,622 | 3/1994 | Dreikorn et al. | 514/311 |

CYCLOALKANE DERIVATIVES

This invention concerns cycloalkane derivatives and more particularly cycloalkane derivatives which are inhibitors of the enzyme 5-lipoxygenase (hereinafter referred to as 5-LO). The invention also concerns processes for the manufacture of said cycloalkane derivatives and pharmaceutical compositions containing them. Also included in the invention is the use of said cycloalkane derivatives in the treatment of various inflammatory and/or allergic diseases in which the direct or indirect products of 5-LO catalysed oxidation of arachidonic acid are involved, and the production of new medicaments for such use.

As stated above the cycloalkane derivatives described hereinafter are inhibitors of 5-LO, which enzyme is known to be involved in catalysing the oxidation of arachidonic acid to give rise via a cascade process to the physiologically active leukotrienes such as leukotriene $B_4$ ($LTB_4$) and the peptido-lipid leukotrienes such as leukotriene $C_4$ ($LTC_4$) and leukotriene $D_4$ ($LTD_4$) and various metabolites.

The biosynthetic relationship and physiological properties of the leukotrienes are summarised by G. W. Taylor and S. R. Clarke in *Trends in Pharmacological Sciences*, 1986, 7, 100–103. The leukotrienes and their metabolites have been implicated in the production and development of various inflammatory and allergic diseases such as inflammation of the joints (especially rheumatoid arthritis, oesteoarthritis and gout), inflammation of the gastrointestinal tract (especially inflammatory bowel disease, ulcerative colitis and gastritis), skin disease (especially psoriasis, eczema and dermatitis) and respiratory disease (especially asthma, bronchitis and allergic rhinitis), and in the production and development of various cardiovascular and cerebrovascular disorders such as myocardial infarction, angina and peripheral vascular disease. In addition the leukotrienes are mediators of inflammatory diseases by virtue of their ability to modulate lymphocyte and leukocyte function. Other physiologically active metabolites of arachidonic acid, such as the prostaglandins and thromboxanes, arise via the action of the enzyme cyclooxygenase on arachidonic acid.

It is known from European Patent Applications Nos. 0375404 and 0385662 that certain 4-alkoxy-4-aryltetrahydropyran and 3-alkoxy-3-aryltetrahydrofuran derivatives are inhibitors of the enzyme 5-LO.

It is further known from European Patent Applications Nos. 0375452 and 0385663 that certain 1-alkoxy-1-arylcycloalkane derivatives are inhibitors of the enzyme 5-LO.

It is further known from European Patent Application No. 0462830 that certain 4-alkyl-4-aryltetrahydropyran derivatives are inhibitors of the enzyme 5-LO.

We have now discovered that, unlike the cycloalkane derivatives disclosed in European Patent Application Nos. 0375452 and 0385663, it is not mandatory to have alkoxy and aryl substituents located at the same carbon atom of the cycloalkane ring. The alkoxy and aryl substituents may be spaced apart around the cycloalkane ring.

We have discovered that the cycloalkane derivatives of the invention are effective as inhibitors of the enzyme 5-LO and thus of leukotriene biosyntheses. Thus, such compounds are of value as therapeutic agents in the treatment of, for example, allergic conditions, psoriasis, asthma, cardiovascular and cerebrovascular disorders, and/or inflammatory and arthritic conditions, mediated alone or in part by one or more leukotrienes.

According to the invention there is provided a cycloalkane derivative of the formula I (set out hereinafter) wherein $Ar^1$ is phenyl or naphthyl, or a 10-membered bicyclic heterocyclic moiety containing one or two nitrogen heteroatoms and optionally containing a further heteroatom selected from nitrogen, oxygen and sulphur, and $Ar^1$ may optionally bear up to four substituents selected from halogeno, hydroxy, cyano, oxo, thioxo, (1–4C)alkyl, (1–4C)alkoxy, fluoro-(1–4C)alkyl, phenyl, benzoyl and phenyl-(1–4C)alkyl and wherein any phenyl, benzoyl or phenyl-(1–4C)alkyl substituent may optionally bear one or two substituents selected from halogeno, (1–4C)alkyl and (1–4C)alkoxy;

$A^1$ is a direct link to $X^1$ or is (1–3C)alkylene;

$X^1$ is oxy, thio, sulphinyl or sulphonyl;

$Ar^2$ is phenylene, pyridylene or pyrimidinylene which may optionally bear one or two substituents selected from halogeno, hydroxy, amino, nitro, cyano, carbamoyl, trifluoromethyl, (1–4C)alkyl and (1–4C)alkoxy;

p is 1 to 4;

q is 0 to 2;

$R^1$ is hydrogen, (1–4C)alkyl, (2–4C)alkenyl or (3–4C)alkynyl;

$R^2$ is hydrogen, hydroxy, (1–4C)alkyl, (1–4C)alkoxy, (2–4C)alkenyloxy or (3–4C)alkynyloxy;

or the $OR^1$ and $R^2$ groups together form a (1–4C)alkylenedioxy, oxo, thioxo, imino, hydroxyimino or (1–4C)alkoxyimino group;

r is 0 to 3; and $R^3$ is halogeno, trifluoromethyl or (1–4C)alkyl;

or a pharmaceutically-acceptable salt thereof.

In a further aspect of the invention there is provided a cycloalkane derivative of the formula I wherein $Ar^1$, $A^1$, $X^1$, $Ar^2$, r, p, q, $R^1$, $R^2$ and $R^3$ have any of the meanings defined above or, in addition, $Ar^2$ is thiophenediyl, furandiyl, thiazolediyl or oxazolediyl which may optionally bear one or two substituents as defined above for substituents on $Ar^2$; or a pharmaceutically-acceptable salt thereof.

The chemical formulae referred to herein by Roman numerals are set out for convenience on a separate sheet hereinafter.

In this specification the generic term "alkyl" includes both straight-chain and branched-chain alkyl groups. However references to individual alkyl groups such as "propyl" are specific for the straight-chain version only and references to individual branched-chain alkyl groups such as "isopropyl" are specific for the branched-chain version only. An analogous convention applies to other generic terms.

It is to be understood that, insofar as certain of the compounds of formula I defined above may exist in optically active or racemic forms by virtue of one or more asymmetric carbon atoms, the invention includes in its definition any such optically active or racemic form which possesses the property of inhibiting 5-LO. The synthesis of optically active forms may be carried out by standard techniques of organic chemistry well known in the art, for example by synthesis from optically active starting materials or by resolution of a racemic form. Similarly, inhibitory properties against 5-LO may be evaluated using the standard laboratory techniques referred to hereinafter.

Suitable values for the generic terms referred to above include those set out below.

A suitable value for $Ar^1$ when it is naphthyl is, for example 1-naphthyl or 2-naphthyl.

A suitable value for $Ar^1$ when it is a 10-membered bicyclic heterocyclic moiety containing one or two nitrogen heteroatoms and optionally containing a further heteroatom selected from nitrogen, oxygen and sulphur is, for example, a 10-membered benzo-fused heterocyclic moiety such as quinolyl, isoquinolyl, cinnolinyl, quinazolinyl, quinoxalinyl, 4H-1,4-benzoxazinyl or 4H-1,4-benzothiazinyl, or a hydrogenated derivative thereof such as 1,2-dihydroquinolyl, 1,2,3,4-tetrahydroquinolyl, 1,2-dihydroisoquinolyl, 2,3-dihydro-4H-1,4-benzoxazinyl or 2,3-dihydro-4H-1,4-benzothiazinyl; or, for example, a 10-membered pyrido-fused heterocyclic moiety such as 1,7-naphthyridinyl, 1,8-naphthyridinyl, pyrido[2,3-d]pyrimidinyl, pyrido[2,3-b]pyrazinyl, 4H-pyrido[3,2-b][1,4]oxazinyl and 4H-pyrido[3,2-b][1,4]thiazinyl, or a hydrogenated derivative thereof.

The heterocyclic moiety may be attached through any available position including from either of the two rings of the bicyclic heterocyclic moiety and including through an available nitrogen atom. The heterocyclic moiety may bear a suitable substituent such as, for example, a (1–4C)alkyl, fluoro-(1–4C)alkyl, phenyl, benzoyl or phenyl-(1–4C)alkyl substituent on an available nitrogen atom.

Suitable values for substituents which may be present on $Ar^1$, $Ar^2$, on the phenyl substituent on $Ar^1$ or on any of the substituents on $Ar^1$ which contain a phenyl group include, for example:

| | |
|---|---|
| for halogeno: | fluoro, chloro, bromo and iodo; |
| for (1–4C)alkyl: | methyl, ethyl, propyl, isopropyl, butyl, isobutyl, sec-butyl and tert-butyl; |
| for (1–4C)alkoxy: | methoxy, ethoxy, propoxy, isopropoxy and butoxy; |
| for fluoro-(1–4C)alkyl: | fluoromethyl, difluoromethyl, trifluoromethyl, 2-fluoroethyl, 2,2,2-trifluoroethyl and pentafluoroethyl; |
| for phenyl-(1–4C)alkyl: | benzyl, phenethyl, 3-phenylpropyl and α-methylbenzyl. |

A suitable value for $A^1$ when it is (1–3C)alkylene is, for example, methylene, ethylene or trimethylene.

A suitable value for $Ar^2$ when it is phenylene is, for example, 1,3-phenylene or 1,4-phenylene; when it is pyridylene is, for example, 3,5-pyridylene; when it is pyrimidinylene is, for example, 4,6-pyrimidinylene; when it is thiophenediyl is, for example, 2,4- or 2,5-thiophenediyl; when it is furandiyl is, for example, 2,4- or 2,5-furandiyl; when it is thiazolediyl is, for example, 2,4- or 2,5-thiazolediyl; and when it is oxazolediyl is, for example, 2,4- or 2,5-oxazolediyl.

A suitable value for $R^1$, $R^2$ or $R^3$ when it is (1–4C)alkyl is for example, methyl, ethyl, propyl, isopropyl or butyl.

A suitable value for $R^1$ when it is (2–4C)alkenyl is, for example, vinyl or allyl; and when it is (3–4C)alkynyl is, for example, 2-propynyl.

A suitable value for $R^2$ when it is (1–4C)alkoxy is, for example, methoxy, ethoxy, propoxy, isopropoxy or butoxy; when it is (2–4C)alkenyloxy is, for example, vinyloxy or allyloxy; and when it is (3–4C)alkynyloxy is, for example, 2-propynyloxy.

When the $OR^1$ and $R^2$ groups together form a (1–4C)alkylenedioxy group, a suitable value is, for example methylenedioxy, ethylenedioxy, trimethylenedioxy or tetramethylenedioxy.

When the $OR^1$ and $R^2$ groups together form a (1–4C)alkoxyimino group, a suitable value is, for example, a methoxyimino or ethoxyimino group.

It will be appreciated that when r is 1 to 3 then a $R^3$ group may be attached to any of the available carbon atoms of the cycloalkane ring including the carbon atom to which the $Ar^2$ group is attached. When r is 2 or 3, two of the $R^3$ groups may be attached to any one of the available carbon atoms of the cycloalkane ring.

A suitable value for $R^3$ when it is halogeno is, for example, fluoro or chloro.

A suitable pharmaceutically-acceptable salt of a novel compound of the invention is, for example, an acid-addition salt of a compound of the invention which is sufficiently basic, for example, an acid-addition salt with, for example, an inorganic or organic acid, for example hydrochloric, hydrobromic, sulphuric, phosphoric, trifluoroacetic, citric or maleic acid. In addition a suitable pharmaceutically-acceptable salt of a novel compound of the invention which is sufficiently acidic is an alkali metal salt, for example a sodium or potassium salt, an alkaline earth metal salt, for example a calcium or magnesium salt, an ammonium salt or a salt with an organic base which affords a physiologically-acceptable cation, for example a salt with methylamine, dimethylamine, trimethylamine, piperidine, morpholine or tris-(2-hydroxyethyl)amine.

Particular compounds of the invention are, for example, cycloalkane derivatives of the formula I wherein:

(a) $Ar^1$ is phenyl or naphthyl which may optionally bear one, two or three substituents selected from any of those substituents on $Ar^1$ defined hereinbefore other than oxo and thioxo; and $A^1$, $X^1$, $Ar^2$, $R^1$, $R^2$, p, q, r, and $R^3$ have any of the meanings defined hereinbefore or in this section concerning particular compounds of the invention;

(b) $Ar^1$ is phenyl or naphth-2-yl which may optionally bear one or two substituents selected from fluoro, chloro, methyl, ethyl, isopropyl, tert-butyl, methoxy, trifluoromethyl, phenyl, benzoyl and benzyl, and wherein said phenyl, benzoyl or benzyl substituents may optionally bear a substituent selected from fluoro, chloro, methyl and methoxy; and $A^1$, $X^1$, $Ar^2$, p, q, r, $R^1$, $R^2$ and $R^3$ have any of the meanings defined hereinbefore or in this section concerning particular compounds of the invention;

(c) $Ar^1$ is a 10-membered benzo-fused heterocyclic moiety containing one or two nitrogen heteroatoms and optionally containing a further heteroatom selected from oxygen and sulphur, which heterocyclic moiety may optionally bear one or two oxo or thioxo substituents and up to two further substituents selected from any of those substituents on $Ar^1$ defined hereinbefore other than oxo or thioxo; and $A^1$, $Ar^2$, p, q, r, $X^1$, $R^1$, $R^2$ and $R^3$ have any of the meanings defined hereinbefore or in this section concerning particular compounds of the invention;

(d) $Ar^1$ is quinolyl, 1,2-dihydroquinolyl, 1,2,3,4-tetrahydroquinolyl or 2,3-dihydro-4H-1,4-benzoxazinyl which may optionally bear one oxo or thioxo substituent and up to two further substituents selected from any of those substituents on $Ar^1$ defined hereinbefore other than oxo or thioxo; and $A^1$, $X^1$, $R^1$, $Ar^2$, p, q, r, $R^2$ and $R^3$ have any of the meanings defined hereinbefore or in this section concerning particular compounds of the invention;

(e) $Ar^1$ is 2-oxo-1,2-dihydroquinolinyl, 2-thioxo-1,2-dihydroquinolinyl, 2-oxo-1,2,3,4-tetrahydroquinolinyl, 2-thioxo-1,2,3,4-tetrahydroquinolinyl or 3-oxo-2,3-dihydro-4H-1,4-benzoxazinyl which may optionally bear up to three substituents selected from any of those substituents on $Ar^1$ defined hereinbefore other than oxo or thioxo; and $A^1$, $X^1$, $Ar^2$, p, q, r, $R^1$, $R^2$ and $R^3$ have any of the meanings defined hereinbefore or in this section concerning particular compounds of the invention;

(f) $Ar^1$ is 2-oxo-1,2-dihydroquinolin-3-yl, 2-oxo-1,2-dihydroquinolin-6-yl, 2-oxo-1,2-dihydroquinolin-7-yl, 3-oxo-2,3-dihydro-4H-1,4-benzoxazin-7-yl or 3-oxo-2,3-dihydro-4H-1,4-benzothiazin-7-yl which may optionally bear up to three substituents selected from any of those substituents on $Ar^1$ defined hereinbefore other than oxo or thioxo; and $A^1$, $X^1$, $Ar^2$, p, q, r, $R^1$, $R^2$ and $R^3$ have any of the meanings defined hereinbefore or in this section concerning particular compounds of the invention;

(g) $A^1$ is a direct link to $X^1$, and $X^1$ is oxy, thio, sulphinyl or sulphonyl; and $Ar^1$, $Ar^2$, p, q, r, $R^1$, $R^2$ and $R^3$ have any of the meanings defined hereinbefore or in this section concerning particular compounds of the invention;

(h) $A^1$ is methylene and $X^1$ is oxy, thio, sulphinyl or sulphonyl; and $Ar^1$, $Ar^2$, p, q, r, $R^1$, $R^2$ and $R^3$ have any of the meanings defined hereinbefore or in this section concerning particular compounds of the invention;

(i) $Ar^2$ is 1,3-phenylene which may optionally bear one or two substituents selected from fluoro, chloro, hydroxy, amino, nitro, methyl, methoxy and trifluoromethyl; and $Ar^1$, $A^1$, $X^1$, p, q, r, $R^1$, $R^2$ and $R^3$ have any of the meanings defined hereinbefore or in this section concerning particular compounds of the invention;

(j) p is 1 to 3 and q is 1 or 2; and $Ar^1$, $A^1$, $X^1$, $Ar^2$, r, $R^1$, $R^2$ and $R^3$ have any of the meanings defined hereinbefore or in this section concerning particular compounds of the invention;

(k) $R^1$ is hydrogen, methyl, ethyl or propyl and $R^2$ is hydrogen, hydroxy, methyl, ethyl, propyl, methoxy, ethoxy or propoxy; and $Ar^1$, $A^1$, $X^1$, $Ar^2$, p, q, r and $R^3$ have any of the meanings defined hereinbefore or in this section concerning particular compounds of the invention;

(l) the $OR^1$ and $R^2$ groups together form a methylenedioxy, ethylenedioxy, trimethylenedioxy or tetramethylenedioxy group; and $Ar^1$, $A^1$, $X^1$, $Ar^2$, p, q, r and $R^3$ have any of the meanings defined hereinbefore or in this section conerning particular compounds of the invention;

(m) the $OR^1$ and $R^2$ groups together form an oxo, imino, hydroxyimino, methoxyimino or ethoxyimino group; and $Ar^1$, $A^1$, $X^1$, $Ar^2$, p, q, r and $R^3$ have any of the meanings defined hereinbefore or in this section concerning particular compounds of the invention;

(n) r is 0, 1 or 2 and $R^3$ is independently fluoro, chloro, methyl, ethyl or propyl; and $Ar^1$, $A^1$, $X^1$, $Ar^2$, p, q, $R^1$ and $R^2$ have any of the meanings defined hereinbefore or in this section concerning particular compounds of the invention; or (o) r is 1 or 2, $R^3$ is independently methyl, ethyl or propyl and at least one $R^3$ group is located on a carbon atom attached to the carbon atom which bears the $Ar^2$ group; and $Ar^1$, $A^1$, $X^1$, $Ar^2$, p, q, $R^1$ and $R^2$ have any of the meanings defined hereinbefore or in this section concerning particular compounds of the invention; or a pharmaceutically-acceptable salt thereof.

Further particular compounds of the invention are, for example, cycloalkane derivatives of the formula I wherein:

(a) r is 1 or 2, $R^3$ is independently methyl or ethyl and at least one $R^3$ group is located on the carbon atom within the $-(CH_2)_p-$ group which is attached to the carbon atom which bears the $Ar^2$ group; and $Ar^1$, $A^1$, $X^1$, $Ar^2$, p, q, $R^1$ and $R^2$ have any of the meanings defined hereinbefore; or (b) r is 1 and $R^3$ is methyl or ethyl which is located on the carbon atom within the $-(CH_2)_p-$ group which is attached to the carbon atom which bears the $Ar^2$ group such that the $R^3$ and $Ar^2$ groups are in a cis-relationship; and $Ar^1$, $A^1$, $X^1$, $Ar^2$, p, q, $R^1$ and $R^2$ have any of the meanings defined hereinbefore; or a pharmaceutically-acceptable salt thereof.

A particular compound of the invention comprises a cycloalkane derivative of the formula I wherein $Ar^1$ is phenyl which may optionally bear a substituent selected from fluoro, chloro, methyl, tert-butyl, phenyl, benzoyl and benzyl and wherein said phenyl, benzoyl or benzyl substituent may optionally bear a fluoro or chloro substitutent, or $Ar^1$ is naphth-2-yl which may optionally bear a substituent selected from fluoro, chloro and methyl;

$A^1$ is a direct link to $X^1$, or is methylene;

$X^1$ is oxy, thio, sulphinyl or sulphonyl;

$Ar^2$ is 1,3-phenylene which may optionally bear one substituent selected from fluoro, chloro and trifluoromethyl;

p is 2 or 3;

q is 1;

$R^1$ is hydrogen, methyl, ethyl or propyl;

$R^2$ is hydrogen, hydroxy, methyl, ethyl, propyl, methoxy, ethoxy or propoxy;

or the $OR^1$ and $R^2$ groups together form an ethylenedioxy, trimethylenedioxy, oxo, hydroxyimino or methoxyimino group;

r is 0, 1 or 2 and $R^3$ is independently methyl, ethyl or propyl;

or a pharmaceutically-acceptable salt thereof.

A further particular compound of the invention comprises a cycloalkane derivative of the formula I wherein $Ar^1$ is 2-oxo-1,2-dihydroquinolinyl, 2-oxo-1,2,3,4-tetrahydroquinolinyl, or 3-oxo-2,3-dihydro-4H-1,4-benzoxazinyl which may optionally bear one, two or three substituents selected from fluoro, chloro, methyl, ethyl, 2-fluoroethyl, phenyl and benzyl;

$A^1$ is a direct link to $X^1$, or is methylene;

$X^1$ is oxy, thio, sulphinyl or sulphonyl;

$Ar^2$ is 1,3-phenylene which may optionally bear one substituent selected from fluoro, chloro and trifluoromethyl;

p is 2 or 3;

q is 1;

$R^1$ is hydrogen, methyl, ethyl or propyl;

$R^2$ is hydrogen, hydroxy, methyl, ethyl, propyl, methoxy, ethoxy or propoxy;

or the $OR^1$ and $R^2$ groups together form an ethylenedioxy, trimethylenedioxy, oxo, hydroxyimino or methoxyimino group;

r is 0, 1 or 2 and $R^3$ is independently methyl, ethyl or propyl;

or a pharmaceutically-acceptable salt thereof.

A preferred compound of the invention comprises a cycloalkane derivative of the formula I wherein
Ar¹ is naphth-2-yl, 1-methyl-2-oxo-1,2-dihydroquinolin-6-yl or 4-methyl-3-oxo-2,3-dihydro-4H-1,4-benzoxazin-7-yl;
A¹ is methylene and X¹ is oxy, or A¹ is a direct link to X¹ and X¹ is thio;
Ar² is 1,3-phenylene or 5-fluoro-1,3-phenylene;
p is 2 or 3;
q is 1;
R¹ is methyl or ethyl;
R² is hydrogen, methoxy or ethoxy;
r is 1 or 2, R³ is independently methyl or ethyl and at least one R³ group is located on the carbon atom within the $—(CH_2)_p—$ group which is attached to the carbon atom which bears the Ar² group;
or a pharmaceutically-acceptable salt thereof.

A further preferred compound of the invention comprises a cycloalkane derivative of the formula I wherein
Ar¹ is 1-methyl-2-oxo-1,2-dihydroquinolin-6-yl;
A¹ is methylene and X¹ is oxy;
Ar² is 1,3-phenylene or 5-fluoro-1,3-phenylene;
p is 3;
q is 1;
R¹ is methyl or ethyl;
R² is methoxy or ethoxy;
r is 1 and R³ is methyl which is located on the carbon atom within the $—(CH_2)_p—$ group which is attached to the carbon atom which bears the Ar² group;
or a pharmaceutically-acceptable salt thereof.

A further preferred compound of the invention comprises a cycloalkane derivative of the formula I wherein
Ar¹ is 1-methyl-2-oxo-1,2-dihydroquinolin-6-yl;
A¹ is methylene and X¹ is oxy;
Ar² is 1,3-phenylene or 5-fluoro-1,3-phenylene;
p is 3;
q is 1;
R¹ is methyl or ethyl;
R² is methoxy or ethoxy;
r is 1 and R³ is methyl which is located on the carbon atom within the $—(CH_2)_p—$ group which is attached to the carbon atom which bears the Ar² group such that the R³ and Ar² groups are in a cis-relationship;
or a pharmaceutically-acceptable salt thereof.

A specific especially preferred compound of the invention is the following compound of the formula I, or a pharmaceutically-acceptable salt thereof:
(3RS,4SR)-1,1-dimethoxy-4-methyl-3-[3-(1-methyl-2-oxo-1,2-dihydroquinolin-6-ylmethoxy)phenyl]cyclohexane or the (3RS,4RS)-isomer thereof,
1-methoxy-4-methyl-3-[3-(1-methyl-2-oxo-1,2-dihydroquinolin-6-ylmethoxy)phenyl]cyclohexane or
(3RS,4SR)-4-methyl-3-[3-(naphth-2-ylmethoxy)-phenyl]cyclohexanone.

A further specific especially preferred compound of the invention is the following compound of the formula I, or a pharmaceutically-acceptable salt thereof:
1,1-dimethoxy-3-[3-(1-methyl-2-oxo-1,2-dihydroquinolin-6-ylmethoxy)phenyl]cyclohexane,
(1SR,3RS,4SR)-1-methoxy-4-methyl-3-[3-(1-methyl-2-oxo-1,2-dihydroquinolin- 6-ylmethoxy)phenyl]cyclohexane or the (1RS,3RS,4SR)-isomer thereof,
(1SR,3RS,4SR)-1,4-dimethyl-1-hydroxy-3-[3-(1-methyl-2-oxo-1,2-dihydroquinolin-6-ylmethoxy)phenyl]-cyclohexane,
(1SR,3RS,4SR)-1,4-dimethyl-1-methoxy-3-[3-(1-methyl-2-oxo-1,2-dihydroquinolin-6-ylmethoxy)phenyl]-cyclohexane,
(3RS,4SR)-4-methyl-3-[3-(1-methyl-2-oxo-1,2-dihydroquinolin-6-ylmethoxy)phenyl]cyclohexanone ethylene acetal or
(3RS,4SR)-1,1-dimethoxy-4-methyl-3-[3-(1-methyl-2-oxo-1,2-dihydroquinolin-6-ylmethoxy)phenyl]cyclopentane.

A compound of the invention comprising a cycloalkane derivative of the formula I, or a pharmaceutically-acceptable salt thereof, may be prepared by any process known to be applicable to the preparation of structurally-related compounds. Suitable procedures are provided hereinafter as a further feature of the invention and are illustrated by the following representative examples in which, unless otherwise stated, Ar¹, A¹, X¹, Ar², p, q, r, R¹, R² and R3 have any of the meanings defined hereinbefore, provided that when there is an amino or hydroxy group in Ar¹, Ar² or R², or the group OR¹ is a hydroxy group, then any such group may optionally be protected by a conventional protecting group which may be removed when so desired by conventional means.

(a) For the production of those compounds of the formula I wherein R¹ is (1–4C)alkyl, (2–4C)alkenyl or (3–4C)alkynyl and R² is (1–4C)alkoxy, (2–4C)alkenyloxy or (3–4C)alkynyloxy, or the OR¹ and R² groups together form a (1–4C)alkylenedioxy group, the reaction, conveniently in the presence of a suitable acid, of a ketone of the formula II with a (1–4C)alkyl, (2–4C)alkenyl or (3–4C)alkynyl alcohol or a suitable derivative thereof, or with a (1–4C)alkylenediol.

A suitable acid for the reaction is, for example, hydrochloric, sulphuric, phosphoric, trifluoroacetic or 4-toluenesulphonic acid, or a Lewis Acid such as a boron trihalide, for example boron trifluoride. Alternatively a suitable acid is provided by an inorganic material, for example a clay such as montmorillonite clay.

A suitable derivative of a (1–4C)alkyl, (2–4C)alkenyl or (3–4C)alkynyl alcohol is, for example an acetal or hemi-acetal formed by the reaction of the alcohol and a suitable aldehyde or ketone such as acetaldehyde, acetone and cyclohexanone, for example an orthoformate, for example a tri-(1–4C)alkyl orthoformate such as trimethyl orthoformate, or for example an orthocarbonate, for example a tetra-(1–4C)alkyl orthocarbonate such as tetramethyl orthocarbonate.

The reaction is conveniently performed in a suitable inert solvent or diluent, for example, one or more of 1,2-dimethoxyethane, tetrahydrofuran, methylene chloride, carbon tetrachloride or a dipolar aprotic solvent such as N,N-dimethylformamide and dimethylsulphoxide. The reaction is conveniently performed at a temperature in the range for example 10° to 150° C., conveniently at or near ambient temperature.

The starting materials of the formula II may be obtained by standard procedures of organic chemistry. The preparation of such starting materials is described within the accompanying non-limiting Examples. Alternatively necessary starting materials are obtainable by analogous procedures to those illustrated which are within the ordinary skill of an organic chemist.

A suitable protecting group for an amino group is, for example, an acyl group for example a (2–4C)alkanoyl group (especially acetyl), a (1–4C)alkoxycarbonyl group (especially methoxycarbonyl, ethoxycarbonyl or tert-butoxycarbonyl), an arylmethoxycarbonyl group (especially benzyloxycarbonyl) or an aroyl group (especially benzoyl). The deprotection conditions for the above protecting groups necessarily vary with the choice of protecting group. Thus, for example, an acyl group such as an alkanoyl or alkoxycarbonyl or an aroyl group may be removed for example, by hydrolysis with a suitable base such as an alkali metal hydroxide, for example lithium or sodium hydroxide. Alternatively an acyl group such as a tert-butoxycarbonyl group may be removed, for example, by treatment with a suitable acid such as hydrochloric, sulphuric or phosphoric acid or trifluoroacetic acid and an arylmethoxycarbonyl group such as a benzyloxycarbonyl group may be removed, for example, by hydrogenation over a catalyst such as palladium-on-charcoal.

A suitable protecting group for a hydroxy group is, for example, an acyl group, for example a (2–4C)alkanoyl group (especially acetyl), an aroyl group (especially benzoyl) or an arylmethyl group (especially benzyl). The deprotection conditions for the above protecting groups will necessarily vary with the choice of protecting group. Thus, for example, an acyl group such as an alkanoyl or an aroyl group may be removed, for example, by hydrolysis with a suitable base such as an alkali metal hydroxide, for example lithium or sodium hydroxide. Alternatively an arylmethyl group such as a benzyl group may be removed, for example, by hydrogenation over a catalyst such as palladium-on-charcoal.

(b) The coupling, preferably in the presence of a suitable base, of a compound of the formula III with a compound of the formula $Ar^1$—$A^1$—Z wherein Z is a displaceable group.

A suitable displaceable group Z is, for example, a halogeno or sulphonyloxy group, for example a fluoro, chloro, bromo, iodo, methanesulphonyloxy or toluene-4-sulphonyloxy group.

A suitable base for the coupling reaction is, for example, an alkali or alkaline earth metal carbonate, (1–4C)alkoxide, hydroxide or hydride, for example sodium carbonate, potassium carbonate, sodium ethoxide, potassium butoxide, sodium hydroxide, potassium hydroxide, sodium hydride or potassium hydride; or an organometallic base such as (1–4C)alkyl-lithium, for example n-butyl-lithium. The coupling reaction is conveniently performed in a suitable inert solvent or diluent, for example N,N-dimethylformamide, N,N-dimethylacetamide, N-methylpyrrolidin-2-one, dimethylsulphoxide, acetone, 1,2-dimethoxyethane or tetrahydrofuran, and at a temperature in the range, for example, 10° to 150° C., conveniently at or near ambient temperature.

The reaction may conveniently be performed in the presence of a suitable catalyst, for example a matallic catalyst, for example palladium (O) or copper (I) such as tetrakis(triphenylphospine)palladium, cuprous chloride or cuprous bromide.

The starting materials of the formula $Ar^1$—$A^1$—Z may be obtained by standard procedures of organic chemistry. Starting materials of the formula III are obtainable by analogous procedures to those illustrated in the accompanying Examples or by modifications thereto which are within the ordinary skill of an organic chemist.

(c) For the production of those compounds of the formula I wherein $X^1$ is a sulphinyl or sulphonyl group the oxidation of a compound of the formula I wherein $X^1$ is a thio group.

A suitable oxidising agent is, for example, any agent known in the art for the oxidation of thio to sulphinyl and/or sulphonyl, for example, hydrogen peroxide, a peracid (such as 3-chloroperoxybenzoic or peroxyacetic acid), an alkali metal peroxysulphate (such as potassium peroxymonosulphate), chromium trioxide or gaseous oxygen in the presence of platinum. The oxidation is generally carried out under as mild conditions as possible and with the required stoichiometric amount of oxidising agent in order to reduce the risk of over oxidation and damage to other functional groups. In general the reaction is carried out in a suitable solvent or diluent such as methylene chloride, chloroform, acetone, tetrahydrofuran or tert-butyl methyl ether and at a temperature, for example, at or near ambient temperature, that is in the range 15° to 35° C. When a compound carrying a sulphinyl group is required a milder oxidising agent may also be used, for example sodium or potassium metaperiodate, conveniently in a polar solvent such as acetic acid or ethanol. It will be appreciated that when a compound of the formula I containing a sulphonyl group is required, it may be obtained by oxidation of the corresponding sulphinyl compound as well as of the corresponding thio compound.

(d) For the production of those compounds of the formula I wherein $Ar^1$ bears an alkyl substituent on an available nitrogen atom, wherein $Ar^2$ bears an alkoxy substituent or wherein $R^1$ is alkyl, alkenyl or alkynyl, the alkylation of a compound of the formula I wherein $Ar^1$ bears a hydrogen atom on said available nitrogen atom, wherein $Ar^2$ bears a hydroxy substituent or wherein $R^1$ is hydrogen.

A suitable alkylating agent is, for example, any agent known in the art for the alkylation of an available nitrogen atom, or of hydroxy to alkoxy, alkenyloxy or alkynyloxy, for example an alkyl halide, for example a (1–4C)alkyl chloride, bromide or iodide, in the presence of a suitable base. A suitable base for the alkylation reaction is, for example, an alkali or alkaline earth metal carbonate, sodium hydroxide, potassium hydroxide, sodium hydride or potassium hydride. The alkylation reaction is preferably performed in a suitable inert solvent or diluent, for example N,N-dimethylformamide, dimethylsulphoxide, acetone, 1,2-dimethoxyethane or tetrahydrofuran, and at a temperature in the range, for example, 10° to 150° C., conveniently at or near ambient temperature.

(e) For the production of those compounds of the formula I wherein $R^1$ is hydrogen and $R^2$ is (1–4C)alkyl, the reaction of a ketone of the formula II with an organometallic reagent of the formula (1–4C)alkyl-M wherein M is an alkali metal or alkaline earth metal such as lithium or calcium or M represents the magnesium halide portion of a conventional Grignard reagent.

The reaction is conveniently performed in a suitable inert solvent or diluent as defined hereinbefore and at a temperature in the range, for example, −100° to +30° C., conveniently in the range −80° C. to ambient temperature.

(f) For the production of those compounds of the formula I wherein $OR^1$ and $R^2$ together form an imino, hydroxyimino or (1–4C)alkoxyimino group, the reaction, conveniently in the presence of a suitable base, of a ketone of the formula II with ammonia, hydroxylamine or a O-(1-4C)alkylhydroxylamine.

A suitable base for the reaction is, for example, an alkali or alkaline earth metal carbonate, (1-4C)alkoxide, (1-4C)alkanoate, hydroxide or hydride, for example sodium carbonate, potassium carbonate, barium carbonate, sodium ethoxide, potassium butoxide, sodium acetate, sodium hydroxide, potassium hydroxide, sodium hydride or potassium hydride. Alternatively a suitable base for the reaction is, for example, an organic amine base such as pyridine, 2,6-lutidine, collidine, 4-dimethylaminopyridine, triethylamine, N-methylmorpholine or diazabicyclo[5.4.0]undec-7-ene.

The reaction is conveniently performed in a suitable inert solvent or diluent, for example, one or more of water, a (1-4C)alcohol such as methanol, ethanol and propanol, pyridine, 1,2-dimethoxyethane, tetrahydrofuran, 1,4-dioxan or a dipolar aprotic solvent such as N,N-dimethylformamide and dimethylsulphoxide. The reaction is conveniently performed at a temperature in the range, for example, 10° to 150° C., conveniently at or near 70° C.

When a pharmaceutically-acceptable salt of a compound of the formula I is required, it may be obtained, for example, by reaction of said compound with a suitable acid or base using a conventional procedure. When an optically active form of a compound of the formula I is required, it may be obtained by carrying out one of the aforesaid procedures using an optically active starting material, or by resolution of a racemic form of said compound using a conventional procedure.

As stated previously, the compounds of the formula I are inhibitors of the enzyme 5-LO. The effects of this inhibition may be demonstrated using one or more of the standard procedures set out below:

a) An in vitro assay system involving incubating a test compound with heparinised human blood, prior to challenge with the calcium ionophore A23187 and then indirectly measuring the inhibitory effects on 5-LO by assaying the amount of $LTB_4$ using specific radioimmunoassays described by Carey and Forder (F. Carey and R. A. Forder, *Prostaglandins, Leukotrienes Med.*, 1986, 22, 57; *Prostaglandins*, 1984, 28, 666; *Brit. J. Pharmacol.* 1985, 84, 34P) which involve the use of a protein-$LTB_4$ conjugate produced using the procedure of Young et alia (*Prostaglandins*, 1983, 26(4), 605-613). The effects of a test compound on the enzyme cyclooxygenase (which is involved in the alternative metabolic pathway for arachidonic acid and gives rise to prostaglandins, thromboxanes and related metabolites) may be measured at the same time using the specific radioimmunoassay for thromboxane $B_2(TxB_2)$ described by Carey and Forder (see above). This test provides an indication of the effects of a test compound against 5-LO and also cyclooxygenase in the presence of blood cells and proteins. It permits the selectivity of the inhibitory effect on 5-LO or cyclooxygenase to be assessed.

b) An ex vivo assay system, which is a variation of test a) above, involving administration to a group of rats of a test compound (usually orally as the suspension produced when a solution of the test compound in dimethylsulphoxide is added to carboxymethylcellulose), blood collection, heparinisation, challenge with A23187 and radioimmunoassay of $LTB_4$ and $TxB_2$. This test provides an indication of the bioavailability of a test compound as an inhibitor of 5-LO or cyclooxygenase.

c) An in vivo system involving measuring the effects of a test compound administered orally against the liberation of $LTB_4$ induced by zymosan within an air pouch generated within the subcutaneous tissue of the back of male rats. The rats are anaesthetised and air pouches are formed by the injection of sterile air (20 ml). A further injection of air (10 ml) is similarly given after 3 days. At 6 days after the initial air injection the test compound is administered (usually orally as the suspension produced when a solution of the test compound in dimethylsulphoxide is added to hydroxypropylmethylcellulose), followed by the intrapouch injection of zymosan (1 ml of a 1% suspension in physiological saline). After 3 hours the rats are killed, the air pouches are lavaged with physiological saline, and the specific radioimmunoassay described above is used to assay $LTB_4$ in the washings. This test provides an indication of inhibitory effects against 5-LO in an inflammatory milieu.

Although the pharmacological properties of the compounds of the formula I vary with structural changes as expected, in general compounds of the formula I possess 5-LO inhibitory effects at the following concentrations or doses in at least one of the above tests a)-c):

Test a): $IC_{50}$ ($LTB_4$) in the range, for example, 0.01–40 μM $IC_{50}$ ($TxB_2$) in the range, for example, 40–200 μM;

Test b): oral $ED_{50}(LTB_4)$ in the range, for example, 0.1–100 mg/kg;

Test c): oral $ED_{50}(LTB_4)$ in the range, for example, 0.1–100 mg/kg.

No overt toxicity or other untoward effects are present in tests b) and/or c) when compounds of the formula I are administered at several multiples of their minimum inhibitory dose or concentration.

Thus, by way of example, the compound 1-methoxy-4-methyl-3-[3-(1-methyl-2-oxo-1,2-dihydroquinolin-6-ylmethoxy)phenyl]cyclohexane has an $IC_{50}$ of 0.39 μM against $LTB_4$ in test (a), and the compound (3RS,4SR)-1,1-dimethoxy-4-methyl-3-[3-(1-methyl-2-oxo-1,2-dihydroquinolin-6-ylmethoxy)phenyl]cyclohexane has an $IC_{50}$ of 0.04 μM against $LTB_4$ in test (a).

These compounds are examples of compounds of the invention which show selective inhibitory properties for 5-LO as opposed to cyclooxygenase, which selective properties are expected to impart improved therapeutic properties, for example, a reduction in or freedom from the gastrointestinal side-effects frequently associated with cyclooxygenase inhibitors such as indomethacin.

According to a further feature of the invention there is provided a pharmaceutical composition which comprises a cycloalkane derivative of the formula I, or a pharmaceutically-acceptable salt thereof, in association with a pharmaceutically-acceptable diluent or carrier.

The composition may be in a form suitable for oral use, for example a tablet, capsule, aqueous or oily solution, suspension or emulsion; for topical use, for example a cream, ointment, gel or aqueous or oily solution or suspension; for nasal use, for example a snuff, nasal spray or nasal drops; for vaginal or rectal use, for example a suppository; for administration by inhalation, for example as a finely divided powder such as a dry powder, a microcrystalline form or a liquid aerosol; for sub-lingual or buccal use, for example a tablet or capsule; or for parenteral use (including intravenous, subcutaneous, intramuscular, intravascular or infusion), for example a sterile aqueous or oily solution or suspension. In general the above compositions may be prepared in a conventional manner using conventional excipients.

The amount of active ingredient (that is a cycloalkane derivative of the formula I, or a pharmaceutically-acceptable salt thereof) that is combined with one or more excipients to produce a single dosage form will necessarily vary depending upon the host treated and the particular route of administration. For example, a formulation intended for oral administration to humans will generally contain, for example, from 0.5 mg to 2 g of active agent compounded with an appropriate and convenient amount of excipients which may vary from about 5 to about 98 percent by weight of the total composition. Dosage unit forms will generally contain about 1 mg to about 500 mg of an active ingredient.

According to a further feature of the invention there is provided a cycloalkane derivative of the formula I, or a pharmaceutically-acceptable salt thereof, for use in a method of treatment of the human or animal body by therapy.

The invention also includes a method of treating a disease or medical condition mediated alone or in part by one or more leukotrienes which comprises administering to a warm-blooded animal requiring such treatment an effective amount of an active ingredient as defined above. The invention also provides the use of such an active ingredient in the production of a new medicament for use in a leukotriene mediated disease or medical condition.

The size of the dose for therapeutic or prophylactic purposes of a compound of the formula I will naturally vary according to the nature and severity of the conditions, the age and sex of the animal or patient and the route of administration, according to well known principles of medicine. As mentioned above, compounds of the formula I are useful in treating those allergic and inflammatory conditions which are due alone or in part to the effects of the metabolites of arachidonic acid arising by the linear (5-LO catalysed) pathway and in particular the leukotrienes, the production of which is mediated by 5-LO. As previously mentioned, such conditions include, for example, asthmatic conditions, allergic reactions, allergic rhinitis, allergic shock, psoriasis, atopic dermatitis, cardiovascular and cerebrovascular disorders of an inflammatory nature, arthritic and inflammatory joint disease, and inflammatory bowel diseases.

In using a compound of the formula I for therapeutic or prophylactic purposes it will generally be administered so that a daily dose in the range, for example, 0.5 mg to 75 mg per kg body weight is received, given if required in divided doses. In general lower doses will be administered when a parenteral route is employed. Thus, for example, for intravenous administration, a dose in the range, for example, 0.5 mg to 30 mg per kg body weight will generally be used. Similarly, for administration by inhalation, a dose in the range, for example, 0.5 mg to 25 mg per kg body weight will be used.

Although the compounds of the formula I are primarily of value as therapeutic agents for use in warm-blooded animals (including man), they are also useful whenever it is required to inhibit the enzyme 5-LO. Thus, they are useful as pharmacological standards for use in the development of new biological tests and in the search for new pharmacological agents.

By virtue of their effects on leukotriene production, the compounds of the formula I have certain cytoprotective effects, for example they are useful in reducing or suppressing certain of the adverse gastrointestinal effects of the cyclooxygenase inhibitory non-steroidal anti-inflammatory agents (NSAIA), such as indomethacin, acetylsalicylic acid, ibuprofen, sulindac, tolmetin and piroxicam. Furthermore, co-administration of a 5-LO inhibitor of the formula I with a NSAIA can result in a reduction in the quantity of the latter agent needed to produce a therapeutic effect, thereby reducing the likelihood of adverse side-effects. According to a further feature of the invention there is provided a pharmaceutical composition which comprises a cycloalkane derivative of the formula I, or a pharmaceutically-acceptable salt thereof as defined hereinbefore, in conjunction or admixture with a cyclooxygenase inhibitory non-steroidal anti-inflammatory agent (such as those mentioned above), and a pharmaceutically-acceptable diluent or carrier.

The cytoprotective effects of the compounds of the formula I may be demonstrated, for example in a standard laboratory model which assesses protection against indomethacin-induced or ethanol-induced ulceration in the gastrointestinal tract of rats.

The compositions of the invention may in addition contain one or more therapeutic or prophylactic agents known to be of value for the disease under treatment. Thus, for example a known platelet aggregation inhibitor, hypolipidemic agent, anti-hypertensive agent, beta-adrenergic blocker or a vasodilator may usefully also be present in a pharmaceutical composition of the invention for use in treating a heart or vascular disease or condition. Similarly, by way of example, an anti-histamine, steroid (such as beclomethasone dipropionate), sodium cromoglycate, phosphodiesterase inhibitor or a beta-adrenergic stimulant may usefully also be present in a pharmaceutical composition of the invention for use in treating a pulmonary disease or condition.

The invention will now be illustrated in the following non-limiting examples in which, unless otherwise stated:

(i) evaporations were carried out by rotary evaporation in vacuo and work-up procedures were carried out after removal of residual solids by filtration;

(ii) operations were carried out at room temperature, that is in the range 18°–25° C. and under an atmosphere of an inert gas such as argon;

(iii) column chromatography (by the flash procedure) and medium pressure liquid chromatography (MPLC) were performed on Merck Kieselgel silica (Art. 9385) or Merck Lichroprep RP-18 (Art. 9303) reversed-phase silica obtained from E. Merck, Darmstadt, W. Germany;

(iv) yields are given for illustration only and are not necessarily the maximum attainable;

(v) the end-products of the formula I have satisfactory microanalyses and their structures were confirmed by NMR and mass spectral techniques; unless otherwise stated, $CDCl_3$ solutions of the end-products of the formula I were used for the determination of NMR spectral data, chemical shift values were measured on the delta scale and the following abbreviations are used: s, singlet; d, doublet; t, triplet; q, quartet; m, multiplet;

(vi) intermediates were not generally fully characterised and purity was assessed by thin layer chromatographic, infra-red (IR) or NMR analysis;

(vii) melting points are uncorrected and were determined using a Mettler SP62 automatic melting point apparatus or an oil-bath apparatus; melting points for the end-products of the formula I were determined after crystallisation from a conventional organic solvent such as ethanol, methanol, acetone, ether or hexane, alone or in admixture; and (viii) the following abbreviations have been used:
THF tetrahydrofuran;
DMF N,N-dimethylformamide;
NMP N-methylpyrrolidin-2-one.

EXAMPLE 1

2-Bromomethylnaphthalene (0.663 g) was added dropwise to a stirred mixture of 3-(3-hydroxyphenyl)-4-methylcyclohex-2-en-1-one (0.606 g), potassium carbonate (0.442 g) and DMF (5 ml). The mixture was stirred at ambient temperature for 16 hours. The mixture was poured into water and acidified to pH6 by the addition of dilute hydrochloric acid solution. The mixture was extracted with diethyl ether. The organic phase was washed with water and with brine, dried (MgSO$_4$) and evaporated. There was thus obtained 4-methyl-3-[3-(naphth-2-ylmethoxy)phenylcyclohex-2-en-1-one as an oil (1.03 g) which was used without further purification.

A mixture of a portion (0.41 g) of the product so obtained, 10% palladium-on-charcoal catalyst (0.1 g), ethyl acetate (5 ml) and methanol (20 ml) was stirred under a 1.3 atmospheres pressure of hydrogen gas for 2 hours. The mixture was filtered and the filtrate was evaporated. The residue was purified by column chromatography using a 19:1 mixture of methylene chloride and diethyl ether as eluent. There was thus obtained (3RS,4SR)-4-methyl-3-[3-(naphth-2-ylmethoxy)-phenyl]cyclohexanone as the predominant component (molar ratio 17:3) of an oil which crystallised on trituration under hexane to give a solid (0.26 g), m.p. 83°–85° C.

NMR Spectrum 0.84 (d, 3H). 1.7–3.0 (m, 7H), 3.1–3.45 (m, 1H), 5.21 (s, 2H), 6.6–8.0 (m, 1H); the minor component being the (3RS,4RS)-isomer identifiable by the NMR doublet signal at 0.77δ.

The 3-(3-hydroxyphenyl)-4-methylcyclohex-2-en-1-one used as a starting material was obtained as follows:

Tert-butyldimethylsilyl chloride (6.15 g) was added to a stirred mixture of 3-hydroxbenzonitrile (4.76 g), imidazole (2.79 g) and DMF (25 ml) and the mixture was stirred at ambient temperature for 16 hours. The mixture was poured into water and acidified to pH5 by the addition of dilute hydrochloric acid solution. The mixture was extracted with diethyl ether. The organic phase was washed with water and with brine, dried (MgSO$_4$) and evaporated. There was thus obtained 3-(tert-butyldimethylsilyloxy)benzonitrile (10 g) as an oil.

A solution of a portion (4.68 g) of the material so obtained in THF (10 ml) was added dropwise to a stirred solution of ethylmagnesium bromide (3M in diethyl ether, 13.3 ml) in THF (20 ml). The mixture was heated to 60° C. for 1 hour. The mixture was cooled to 0° C. and the excess of Grignard reagent was hydrolysed by the dropwise addition of 0.5M aqueous hydrochloric acid solution. The mixture was stirred at ambient temperature for 10 minutes. The mixture was extracted with diethyl ether. The organic phase was washed with water and with brine, dried (MgSO$_4$) and evaporated. The residue was purified by column chromatography using a 4:1 mixture of methylene chloride and petroleum ether (b.p. 40°–60° C.) as eluent. There was thus obtained 3-(tert-butyldimethylsilyloxy)phenyl ethyl ketone as a liquid (5.74 g).

A solution of methyl vinyl ketone (0.28 g) in THF (5 ml) was added to a stirred mixture of a portion (1.06 g) of the ketone so obtained, sodium methoxide (0.022 g) and THF (10 ml). The mixture was stirred at ambient temperature for 1 hour. A second portion (0.022 g) of sodium methoxide and a second portion (0.28 g) of methyl vinyl ketone were added in turn and the resultant mixture was stirred at ambient temperature for 3 hours. The mixture was partitioned between ethyl acetate and 2M aqueous hydrochloric acid solution. The organic phase was washed with water and with brine, dried (MgSO$_4$) and evaporated. The residue was dissolved in THF (10 ml) and tetrabutylammonium fluoride (1M in THF, 2 ml) was added. The resultant mixture was stirred at ambient temperature for 15 minutes. The mixture was partitioned between ethyl acetate and water. The organic phase was washed with water and with brine, dried (MgSO$_4$) and evaporated. The residue was purified by column chromatography using a 9:1 mixture of methylene chloride and diethyl ether as eluent. There was thus obtained 1-(3-hydroxyphenyl)-2-methylhexan-1,5-dione as an oil (0.285 g).

A mixture of the material so obtained, 2M aqueous sodium hydroxide (2 ml) and methanol (5 ml) was stirred and heated to 50° C. for 20 minutes. The mixture was cooled to ambient temperature and acidified to pH6 by the addition of dilute hydrochloric acid solution. The mixture was extracted with diethyl ether. The organic phase was washed with water and with brine, dried (MgSO$_4$) and evaporated. The residue was purified by column chromatography using a 9:1 mixture of methylene chloride and diethyl ether as eluent. There was thus obtained 3-(3-hydroxyphenyl)-4-methylcyclohex-2-en-1-one as an oil (0.1 g) which crystallised on trituration under a mixture of hexane and diethyl ether, m.p. 96°–97° C.

EXAMPLE 2

Methyl iodide (0.133 g) and sodium hydride (60% w/w dispersion in mineral oil, 0.021 g) were added in turn to a stirred mixture of 4-methyl-3-[3-(1-methyl-2-oxo-1,2-dihydroquinolin-6ylmethoxy)phenyl]cyclohexan-1-ol (0.177 g) and NMP (1 ml). The mixture was stirred at ambient temperature for 1 hour. A second portion of sodium hydride (60% dispersion, 0.021 g) was added and the mixture was stirred for 1 hour. The mixture was poured into water, acidified to pH5 by the addition of dilute hydrochloric acid solution and extracted with ethyl acetate. The organic phase was washed with water and with brine, dried (MgSO$_4$) and evaporated. The residue was purified by column chromatography using a 1:1 mixture of methylene chloride and diethyl ether as eluent. There was thus obtained 1-methoxy-4-methyl-3-[3-(1-methyl-2-oxo-1,2-dihydroquinolin-6-ylmethoxy)phenyl]cyclohexane as a glass (0.152 g).

NMR Spectrum 0.65 (d, 3H), 1.1–2.35 (m, 7H), 2.7–3.05 (m, 1H), 3.1–3.5 (m and 2s's, 4H), 3.73 (s, 3H), 5.1 (s, 2H), 6.15–7.75 (m, 9H).

The 4-methyl-3-[3-(1-methyl-2-oxo-1,2-dihydroquinolin-6-ylmethoxy)phenyl]cyclohexan-1-ol used as a starting material was obtained as follows:

6-Bromomethyl-1-methyl-1,2-dihydroquinolin-2-one (0.126 g; European Patent Application No. 0385662, Example 6 thereof) was added to a stirred mixture of 3-(3-hydroxyphenyl)-4-methylcyclohex-2-en-1-one (0.1 g), potassium carbonate (0.083 g) and DMF (1.5 ml). The mixture was stirred at ambient temperature for 6 hours. The mixture was poured into water, acidified to pH6 by the addition of dilute hydrochloric acid solution and extracted with ethyl acetate. The organic phase was washed with water and with brine, dried (MgSO$_4$) and evaporated. The residue was purified by column chromatography using initially a 7:3 mixture of methylene chloride and diethyl ether and then a 97:3 mixture of diethyl ether and methanol as eluent. There was thus obtained 4-methyl-3-3-(1-methyl-2-oxo-1,2-dihydroquinolin-6-ylmethoxy)phenyl]cyclohex-2-en-1-one as a foam (0.15 g).

NMR Spectrum 1.17 (d, 3H), 1.5–2.7 (m, 4H), 2.9–3.3 (m, 1H), 3.72 (s, 3H), 5.14 (s, 2H), 6.22 (s, 1H), 6.6–7.8 (m, 9H).

After repetition of the reaction above, a mixture of the product so obtained (0.317 g), platinum oxide (0.06 g) and methanol (10 ml) was stirred under an atmosphere of hydrogen gas for 30 minutes. The mixture was filtered and the filtrate was evaporated. The residue was purified by column chromatography using a 3:2 mixture of methylene chloride and diethyl ether as eluent. There was thus obtained 4-methyl-3-[3-(1-methyl-2-oxo-1,2-dihydroquinolin-6-ylmethoxy)phenyl]cyclohexanone as a foam (0.17 g).

NMR Spectrum 0.78 and 0.85 (2 d's, 3H), 1.75–3.0 (m, 7H), 3.1–3.5 (m, 1H), 3.78 (s, 3H), 5.17 (s, 2H), 7.6–8.8 (m, 9H).

After repetition of the above reactions, sodium borohydride (0.038 g) was added portionwise to a stirred mixture of the cyclohexanone (0.375 g) so obtained, cerous (III) chloride (0.247 g) and methanol (3.75 ml). The mixture was stirred at ambient temperature for 15 minutes. The mixture was partitioned between ethyl acetate and water. The organic phase was washed with water and with brine, dried (MgSO$_4$) and evaporated. The residue was purified by column chromatography using a 12:9:1 mixture of methylene chloride, diethyl ether and methanol as eluent. There was thus obtained 4-methyl-3-[3-(1-methyl-2-oxo-1,2-dihydroquinolin-6-ylmethoxy)phenyl]cyclohexan-1-ol as a foam (0.23 g).

NMR Spectrum 0.61 (d, 3H), 1.1–2.26 (m, 7H), 2.7–3.05 (m, 1H), 3.8–3.95 (m, 4H), 5.11 (s, 2H), 6.65–7.75 (m, 9H).

EXAMPLE 3

Trimethyl orthoformate (1 ml) was added to montmorillonite clay (0.65 g). The mixture was shaken for 5 minutes and then filtered. The solid so obtained was added to a solution of (3RS,4RS)-4-methyl-3-[3-(1-methyl-2-oxo-1,2-dihydroquinolin-6ylmethoxy)-phenyl]cyclohexanone (0.14 g) in carbon tetrachloride (2 ml) and the resultant mixture was stirred at ambient temperature for 20 hours. The mixture was basified by the addition of sodium bicarbonate, filtered and partitioned between ethyl acetate and water. The organic phase was washed with a saturated aqueous sodium bicarbonate solution and with brine, dried (MgSO$_4$) and evaporated. There was thus obtained (3RS,4RS)-1,1-dimethoxy-4-methyl-3-[3-(1-methyl-2-oxo-1,2-dihydroquinolin-6-ylmethoxy)phenyl]cyclohexane as an oil which crystallised on trituration under a mixture of hexane and diethyl ether to give a solid (0.085 g), m.p. 130°–131° C.

NMR Spectrum 0.70 (d, 3H), 1.1–2.6 (m, 8H), 3.19 (s, 6H), 3.73 (s, 3H), 5.11 (s, 2H), 6.6–7.75 (m, 9H).

The (3RS,4RS)-4-methyl-3-[3-(1-methyl-2-oxo-1,2-dihydroquinolin-6-ylmethoxy)phenyl]cyclohexanone used as a starting material was obtained as follows:

Magnesium (0.48 g) and dibromomethane (2 drops) were added in turn to a stirred solution of 3-(naphth-2-ylmethoxy)bromobenzene (6.26 g) in THF (25 ml). The mixture was heated to reflux for 1 minute, stirred at ambient temperature for 30 minutes and then heated to 50° C. for 30 minutes. The mixture was cooled to 0° C. and methylene chloride (0.4 g) was added, followed by a solution of 4-methylcyclohex-2-en-1-one (1.15 g; J. Amer. Chem. Soc. 1974, 96, 215) in diethyl ether (5 ml). The mixture was stirred at ambient temperature for 1 hour. The mixture was poured into water, acidified to pH5 by the addition of dilute hydrochloric acid solution and extracted with diethyl ether. The organic phase was washed with water and with brine, dried (MgSO$_4$) and evaporated. The residue was purified by column chromatography using methylene chloride as eluent. There was thus obtained (3RS,4RS)-4-methyl-3-[3-(naphth-2-ylmethoxy)phenyl]cyclohexanone as an oil which crystallised on trituration under a mixture of petroleum ether (b.p. 40°–60° C.) and diethyl ether to give a solid (1.7 g), m.p. 90°–91° C.

NMR Spectrum 0.74 (d, 3H), 1.25–2.7 (m, 8H), 5.22 (s, 2H), 6.7–8.0 (m, 1H).

A mixture of a portion (0.172 g) of the cyclohexanone so obtained and trimethyl orthoformate: montmorillonite clay complex [prepared by mixing the clay (0.65 g) and trimethyl orthoformate (1 ml) for 5 minutes followed by filtration to give the solid clay complex] was stirred at ambient temperature for 1 hour. The mixture was basified by the addition of sodium bicarbonate, filtered and partitioned between diethyl ether and water. The organic phase was washed with a saturated aqueous sodium bicarbonate solution and with brine, dried (MgSO$_4$) and evaporated. The residue was purified by column chromatography using a 17:3 mixture of ethyl acetate and petroleum ether (b.p. 40°–60° C.) as eluent. There was thus obtained (3RS,4RS)-1,1-dimethoxy-4-methyl-3-[3-(naphth-2-ylmethoxy)phenyl]cyclohexane as an oil (0.275 g).

NMR Spectrum 0.69 (d, 3H), 1.05–2.5 (m, 8H), 3.18 (s, 6H), 5.20 (s, 2H), 6.85–8.0 (m, 11H).

A mixture of the material so obtained, 10% palladium-on-charcoal catalyst (0.07 g), ethyl acetate (20 ml) and methanol (20 ml) was stirred under 2.6 atmospheres pressure of hydrogen gas for 4 hours. The mixture was filtered and the filtrate was evaporated. There was thus obtained (3RS,4RS)-3-hydroxyphenyl-4-methylcyclohexanone in 100% yield as an oil.

6-Bromomethyl-1-methyl-1,2-dihydroquinolin-2-one (0.177 g) was added to a stirred mixture of the cyclohexanone so obtained, potassium carbonate (0.116 g) and DHF (1 ml). The mixture was stirred at ambient temperature for 2 hours. The mixture was poured into water and extracted with ethyl acetate. The organic phase was washed with water and with brine, dried (MgSO$_4$) and evaporated. The residue was purified by column chromatography using a 3:2 mixture of methylene chloride and diethyl ether as eluent. There was thus obtained (3RS,4RS)-4-methyl-3-[3-(1-methyl-2-oxo-1,2-dihydroquinolin-6-ylmethoxy)phenyl]cyclohexanone as an oil (0.22 g).

NMR Spectrum 0.79 (d, 3H), 1.2–2.7 (m, 8H), 3.72 (s, 3H), 5.11 (s, 2H), 6.8–7.75 (m, 9H).

EXAMPLE 4

The procedure described in Example 3 was repeated except that (3RS,4SR)-4-methyl-3-[3-(1-methyl-2-oxo-1,2-dihydroquinolin-6-ylmethoxy)phenyl]cyclohexanone was used in place of the corresponding (3RS,4RS)-isomer. There was thus obtained (3RS,4SR)-

1,1-dimethoxy-4-methyl-3-[3-(1-methyl-2-oxo-1,2-dihydroquinolin-6-ylmethoxy)phenyl]cyclohexane, m.p. 94°–95° C.;

NMR Spectrum 0.69 (d, 3H), 1.2–2.4 (m, 7H), 2.95 (m, 1H), 3.17 (s, 3H), 3.25 (s, 3H), 3.73 (s, 3H), 5.11 (s, 2H), 6.6–7.75 (m, 9H).

The (3RS,4SR)-4-methyl-3-[3-(1-methyl-2-oxo-1,2-dihyroquinolin-6-ylmethoxy)phenyl]cyclohexanone used as a starting material was obtained as follows:

A mixture of (3RS,4SR)-4-methyl-3-[3-(naphth-2-yl-methoxy)phenyl]cyclohexanone (0.215 g; from Example 1 hereinbefore) and trimethyl orthoformate: montmorillonite clay complex [prepared by mixing the clay (0.6 g) and trimethyl orthoformate (1 ml) for 5 minutes followed by filtration to give the solid clay complex] was stirred at ambient temperature for 1 hour. The mixture was filtered and the solid was washed with diethyl ether. The combined filtrate and washings were washed with a saturated aqueous sodium bicarbonate solution and with brine, dried (MgSO$_4$) and evaporated. There was thus obtained (3RS,4SR)-1,1-dimethoxy-4-methyl-3-[3-(naphth-2ylmethoxy)phenyl]cyclohexane as an oil (0.25 g).

A mixture of the material so obtained, 10% palladium-on-charcoal catalyst (0.07 g), ethyl acetate (5 ml) and methanol (10 ml) was stirred under 2.3 atmospheres pressure of hydrogen gas for 5 hours. The mixture was filtered and the filtrate was evaporated. There was thus obtained (3RS,4SR)-3-hydroxyphenyl-4-methylcyclohexanone as an oil (0.129 g).

6-Bromomethyl-1-methyl-1,2-dihydroquinolin-2-one (0.166 g) was added to a stirred mixture of the cyclohexanone so obtained, potassium carbonate (0.099 g) and DMF (1 ml). The mixture was stirred at ambient temperature for 2 hours. The mixture was poured into water and extracted with ethyl acetate. The organic phase was washed with water and with brine, dried (MgSO$_4$) and evaporated. The residue was purified by column chromatography using a 3:2 mixture of methylene chloride and diethyl ether as eluent. There was thus obtained (3RS,4SR)-4-methyl-3-[3-(1-methyl-2-oxo-1,2-dihydroquinolin-6ylmethoxy)phenyl]cyclohexanone as a foam (0.15 g).

NMR Spectrum 0.86 (d, 3H), 1.7–3.0 (m, 7H), 3.25 (m, 1H), 3.73 (s, 3H), 5.11 (s, 2H), 6.6–7.75 (m, 9H).

EXAMPLE 5

6-Bromomethyl-1-methyl-1,2-dihydroquinolin-2-one (0.262 g) was added to a stirred mixture of 1,1-dimethoxy-3-(3-hydroxyphenyl)cyclohexane (0.236 g), potassium carbonate (0.166 g) and DMF (3 ml). The mixture was stirred at ambient temperature for 16 hours. The mixture was poured into water, acidified to pH6 by the addition of dilute hydrochloric acid solution and extracted with ethyl acetate. The organic phase was washed with water and with brine, dried (MgSO$_4$) and evaporated. The residue was purified by column chromatography using a 3:2 mixture of methylene chloride and diethyl ether as eluent. There was thus obtained 1,1-dimethoxy-3-[3-(1-methyl-2-oxo-1,2-dihydroquinolin-6-ylmethoxy)phenyl]cyclohexane (0.3 g, 74%), m.p. 106°–107° C.

NMR Spectrum 1.25–2.25 (m, 8H), 2.73 (m, 1H), 3.20 (s, 3H), 3.22 (s, 3H), 3.74 (s, 3H), 5.11 (s, 2H), 6.7–7.75 (m, 9H).

The 1,1-dimethoxy-3-(3-hydroxyphenyl)cyclohexane used as a starting material was obtained as follows:

Magnesium (0.24 g) and dibromoethane (1 drop) were added in turn to a stirred solution of 3-benzyloxy-bromobenzene (2.63 g; prepared conventionally from benzyl bromide and 3-bromophenol) in THF (15 ml). The mixture was heated to 50° C. for 90 minutes. The mixture was cooled to 0° C. Cuprous chloride (0.2 g) and cyclohex-2-en-1-one (0.96 g) were added in turn. The mixture was stirred at 0° C. for 30 minutes and at ambient temperature for a further 30 minutes. A saturated aqueous ammonium chloride solution was added and the mixture was stirred at ambient temperature for 10 minutes. The mixture was extracted with diethyl ether. The organic phase was washed with brine, dried and evaporated. The residue was purified by column chromatography using a 39:1 mixture of methylene chloride and diethyl ether as eluent. There was thus obtained 3-(3-benzyloxyphenyl)cyclohexanone (0.85 g, 30%), m.p. 55°–57° C.

NMR Spectrum 1.5–2.75 (m, 8H), 2.95 (m, 1H), 5.06 (s, 2H), 6.65–7.5 (m, 9H).

Trimethyl orthoformate (2 ml) was added to montmorillonite clay (1.3 g) and the mixture was shaken for 5 minutes and then filtered. The solid so obtained was added to a solution of 3-(3-benzyloxyphenyl)cyclohexanone (0.28 g) in carbon tetrachloride (4 ml) and the resultant mixture was stirred at ambient temperature for 20 hours. The mixture was basified by the addition of sodium bicarbonate (0.05 g) and filtered. The filtrate was evaporated to give 3-(3-benzyloxyphenyl)-1,1-dimethoxycyclohexane as an oil (0.326 g) which was used without further purification.

A mixture of the material so obtained, 10% palladium-on-charcoal catalyst (0.05 g) and methanol (15 ml) was stirred under 5 atmospheres pressure of hydrogen for 4 hours. Sodium bicarbonate (10 mg) was added. The mixture was filtered and the filtrate was evaporated. There was thus obtained 1,1-dimethoxy-3-(3hydroxyphenyl)cyclohexane as an oil (0.236 g) which was used without further purification.

EXAMPLE 6

6-Bromomethyl-1-methyl-1,2-dihydroquinolin-2-one (0.113 g) was added to a stirred solution of (1SR,3RS,4SR)-3-(3-hydroxyphenyl)-1-methoxy-4-methylcyclohexane (0.097 g), potassium carbonate (0.074 g) and DMF (1.5 ml). The mixture was stirred at ambient temperature for 17 hours. A second portion of potassium carbonate (0.074 g) and of 6-bromomethyl-1-methyl-1,2-dihydroquinolin-2-one (0.033 g) were added and the mixture was stirred at ambient temperature for 5 hours. The mixture was partitioned between ethyl acetate and water. The organic phase was washed with water and with brine, dried (MgSO$_4$) and evaporated. The residue was purified by column chromatography using initially a 1:1 mixture of petroleum ether and diethyl ether and then a 7:3 mixture of methylene chloride and diethyl ether as eluent. There was thus obtained (1SR,3RS,4SR)-1-methoxy-4-methyl-3-[3-(1-methyl-2-oxo-1,2-dihydroquinolin-6-ylmethoxy)-phenylcyclohexane as a foam (0.07 g, 40%).

NMR Spectrum 0.61 (d, 3H), 1.3–1.4 (m, 1H), 1.45–1.75 (m, 2H), 1.8–2.05 (m, 4H), 3.1–3.2 (m, 1H), 3.25 (s, 3H), 3.5–3.6 (m, 1H), 3.67 (s, 3H), 5.04 (s, 2H), 6.6–6.8 (m, 4H), 7.1–7.4 (m, 2H), 7.5–7.65 (m, 3H).

The (1SR,3RS,4SR)-3-(3-hydroxyphenyl)-1-methoxy-4-methylcyclohexane used as a starting material was obtained as follows:

A solution of 3-benzyloxybenzonitrile (14.63 g; prepared conventionally by the reaction of 3-hydroxybenzonitrile and benzyl bromide) in THF (42 ml) was added dropwise to a stirred solution of ethylmagnesium bromide (3M in diethyl ether, 40 ml) in THF (67 ml). The mixture was heated to 60° C. for 1 hour. The mixture was cooled to 0° C. and the excess of Grignard reagent was hydrolysed by the dropwise addition of 6N aqueous hydrochloric acid solution. The mixture was stirred at ambient temperature for 15 minutes. The mixture was extracted with diethyl ether. The organic phase was washed with water and with brine, dried (MgSO$_4$) and evaporated. There was thus obtained 3-benzyloxyphenyl ethyl ketone as a liquid (15.8 g, 94%) which was used without further purification.

Methyl vinyl ketone (5.5 ml) was added dropwise to a mixture of 3-benzyloxyphenyl ethyl ketone (15.7 g), sodium methoxide (0.353 g) and THF (45 ml) which was stirred and heated to 75° C. The mixture was heated to 75° C. for 1 hour. A second portion (0.178 g) of sodium methoxide and a second portion (5.5 ml) of methyl vinyl ketone were added in turn and the mixture was heated to 75° C. for 3 hours. The mixture was cooled to ambient temperature and partitioned between diethyl ether and water. The organic phase was washed with water and with brine, dried (MgSO$_4$) and evaporated. The residue was purified by column chromatography using a 97:3 mixture of methylene chloride and diethyl ether as eluent. There was thus obtained 3-(3-benzyloxyphenyl)-4-methylcyclohex-2-en-1-one as an oil (8.7 g, 46%).

A mixture of a portion (5.4 g) of the material so obtained, 5% palladium-on-charcoal catalyst (0.54 g), ethyl acetate (5 ml) and ethanol (100 ml) was stirred under 1.5 atmospheres pressure of hydrogen for 45 minutes. The mixture was filtered and the filtrate was evaporated. The residue was purified by column chromatography using a 3:2 mixture of petroleum ether and diethyl ether as eluent. There were thus obtained in turn:

(3RS,4SR)-3-(3-benzyloxyphenyl)-4-methylcyclohexanone as an oil (0.934 g), and
(3RS,4SR)-3-(3-hydroxyphenyl)-4-methylcyclohexanone as a solid (0.282 g).

Lithium tri-(1,2-dimethylpropyl)borohydride (1M solution in THF, 1.25 ml) was added dropwise to a solution of (3RS,4SR)-3-(3-benzyloxyphenyl)-4-methylcyclohexanone (0.36 g) in THF (8 ml) which had been cooled to −70° C. The mixture was stirred at −70° C. for 1 hour and then allowed to warm to 0° C. A 2N aqueous sodium hydroxide solution (1 ml) and hydrogen peroxide (1 ml) were added dropwise in turn and the mixture was stirred at ambient temperature for 10 minutes. The mixture was partitioned between diethyl ether and dilute aqueous hydrochloric acid. The organic phase was washed with a saturated aqueous solution of sodium thiosulphate and with brine, dried (MgSO$_4$) and evaporated. The residue was purified by column chromatography using a 19:1 mixture of methylene chloride and ethyl acetate as eluent. There was thus obtained (1SR,3RS,4SR)-3-(3-benzyloxyphenyl)-4-methylcyclohexan-1-ol as an oil (0.269 g, 77%).

NMR Spectrum 0.68 (d, 3H), 1.2–1.35 (m, 1H), 1.4–1.6 (m, 2H), 1.7–1.85 (m, 2H), 2.0–2.2 (m, 2H), 3.25–3.35 (m, 1H), 4.25 (m, 1H), 5.05 (s, 2H), 6.75–6.85 (m, 2H), 7.15–7.45 (m, 7H).

Using an analogous procedure to that described in Example 2, (1SR,3RS,4SR)-3-(3-benzyloxyphenyl)-4-methylcyclohexan-1-ol was reacted with methyl iodide to give (1SR,3RS,4SR)-3-(3-benzyloxyphenyl)-1-methoxy-4-methylcyclohexane in 65% yield as an oil.

A mixture of the material so obtained (0.15 g), 10% palladium-on-charcoal catalyst (0.03 g), ethyl acetate (1 ml) and methanol (10 ml) was stirred under 5 atmospheres pressure of hydrogen for 20 hours. The mixture was filtered and the filtrate was evaporated. There was thus obtained (1SR,3RS,4SR)-3-(3-hydroxyphenyl)-1-methoxy-4-methylcyclohexane as an oil (0.097 g, 97%).

EXAMPLE 7

Using an analogous procedure to that described in Example 2, (1RS,3RS,4SR)-4-methyl-3-[3-(1-methyl-2-oxo-1,2-dihydroquinolin-6-ylmethoxy)phenyl]cyclohexan-1-ol was reacted with methyl iodide to give (1RS,3RS,4SR)-1-methoxy-4-methyl-3-[3-(1-methyl-2-oxo-1,2-dihydroquinolin-6-ylmethoxy)phenyl]cyclohexane as a foam in 60% yield.

NMR Spectrum 0.59 (d, 3H), 1.3–1.42 (m, 1H), 1.6–2.1 (m, 6H), 2.77 (m, 1H), 3.18 (m, 1H), 3.33 (s, 3H), 3.67 (s, 3H), 5.05 (s, 2H), 6.6–6.8 (m, 4H), 7.1–7.2 (m, 1H), 7.25–7.28 (m, 1H), 7.5–7.62 (m, 3H).

The (1RS,3RS,4SR)-4-methyl-3-[3-(1-methyl-2-oxo-1,2-dihydroquinolin-6-ylmethoxy)phenyl]cyclohexan-1-ol used as a starting material was obtained as follows:

Using an analogous procedure to that described in Example 5, 6-bromomethyl-1-methyl-1,2-dihydroquinolin-2-one was reacted with (3RS,4SR)-3-(3-hydroxyphenyl)-4-methylcyclohexanone to give (3RS,4SR)-4-methyl-3-[3-(1-methyl-2-oxo-1,2-dihydroquinolin-6ylmethoxy)phenyl cyclohexanone as a foam in 97% yield.

NMR Spectrum 0.86 (d, 3H), 1.8–2.0 (m, 2H), 2.25–2.6 (m, 4H), 2.7–2.81 (m, 1H), 3.2–3.3 (m, 1H), 3.73 (s, 3H), 5.11 (s, 2H), 6.7–6.9 (m, 4H), 7.2–7.4 (m, 2H), 7.6–7.7 (m, 3H).

Lithium tri-tert-butoxyaluminium hydride (1M solution in THF, 0.55 ml) was added dropwise to a stirred solution of (3RS,4SR)-4-methyl-3-[3-(1-methyl-2-oxo-1,2-dihydroquinolin-6-ylmethoxy)phenyl]cyclohexanone (0.187 g) in THF (3 ml) which had been cooled to −70° C. The mixture was stirred at −70° C. for 1 hour and a second portion (0.1 ml) of the hydride reducing agent was added. The mixture was stirred at −70° C. for a further hour. The mixture was partitioned between ethyl acetate and water. The organic phase was washed with water and with brine, dried (MgSO$_4$) and evaporated. The residue was purified by column chromatography using ethyl acetate as eluent. There was thus obtained (1RS,3RS,4SR)-4-methyl-3-[3-(1-methyl-2-oxo-1,2-dihydroquinolin-6-ylmethoxy)phenyl]cyclohexan-1-ol as a foam (0.127 g, 68%).

NMR Spectrum 0.55–0.65 (d, 3H), 1.25–2.1 (m, 7H), 2.8–2.85 (m, 1H), 3.6–3.75 (s & m, 4H), 5.12 (s, 2H), 6.65–6.85 (m, 4H), 7.1–7.4 (m, 2H), 7.55–7.65 (m, 3H).

EXAMPLE 8

A methyl lithium: lithium bromide complex (1.5M in diethyl ether, 1.36 ml) was added dropwise to a stirred solution of (3RS,4SR)-4-methyl-3-[3-(1-methyl-2-oxo-1,2-dihydroquinolin-6-ylmethoxy)phenyl]cyclohexanone (0.637 g) in THF (10 ml) which had been cooled to −70° C. The mixture was allowed to warm to ambient temperature and was stirred for 1 hour. The mixture was recooled to −70° C. and a second portion of methyl lithium: lithium bromide complex (0.57 ml) was added. The mixture was allowed to warm to ambient temperature and was stirred for 1 hour. The mixture was recooled to −70° C. and a third portion of methyl lithium: lithium bromide complex (0.57 ml) was added. The mixture was allowed to warm to ambient temperature and was stirred for 6 hours. The mixture was partitioned between ethyl acetate and water. The organic phase was washed with water and with brine, dried (MgSO₄) and evaporated. The residue was purified by column chromatography using a 4:1 mixture of methylene chloride and acetone as eluent. There were thus obtained in turn: (1RS,3RS,4SR)-1,4-dimethyl-1-hydroxy-3-[3-(1-methyl-2-oxo-1,2-dihydroquinolin-6-ylmethoxy)phenyl]cyclohexane as a foam (0.109 g, 17%).

NMR Spectrum 0.66 (d, 3H), 1.33 (s, 3H), 1.5–1.8 (m, 6H), 1.97–2.1 (m, 1H), 2.89–2.94 (m, 1H), 3.73 (s, 3H), 5.11 (s, 2H), 6.7–6.83 (m, 4H), 7.15–7.28 (m, 1H), 7.35–7.4 (m, 1H), 7.6–7.7 (m, 3H); and (1SR,3RS,4SR)-1,4-dimethyl-1-hydroxy-3-[3-(1-methyl-2-oxo-1,2-dihydroquinolin-6-ylmethoxy)phenyl]cyclohexane as a foam (0.089 g, 13%).

NMR Spectrum 0.63 (d, 3H), 1.31 (s, 3H), 1.65–1.70 (m, 4H), 1.82–2.2 (m, 3H), 3.2–3.3 (m, 1H), 3.72 (s, 3H), 5.10 (s, 2H), 6.7–6.83 (m, 4H), 7.15–7.29 (m, 1H), 7.35–7.40 (d, 1H), 7.6–7.7 (m, 3H).

EXAMPLE 9

Using an analogous procedure to that described in Example 2, (1SR,3RS,4SR)-1,4-dimethyl-1-hydroxy-3-[3-(1-methyl-2-oxo-1,2-dihydroquinolin-6-ylmethoxy)phenyl]cyclohexane was reacted with methyl iodide to give (1SR,3RS,4SR)-1,4-dimethyl-1-methoxy-3-[3-(1-methyl-2-oxo-1,2-dihydroquinolin-6-ylmethoxy)phenyl]cyclohexane as an oil in 58% yield.

NMR Spectrum 0.63 (d, 3H), 1.19 (s, 3H), 1.39–1.47 (m, 2H), 1.6–2.07 (m, 5H), 3.17 (s & m, 4H), 3.74 (s, 3H), 5.11 (s, 2H), 6.72–6.81 (m, 4H), 7.19–7.23 (m, 1H), 7.37–7.40 (d, 1H), 7.64–7.69 (m, 3H).

EXAMPLE 10

Using an analogous procedure to that described in Example 2, (1RS,3RS,4SR)-1,4-dimethyl-1-hydroxy-3-[3-(1-methyl-2-oxo-1,2-dihydroquinolin-6-ylmethoxy)phenyl]cyclohexane was reacted with methyl iodide to give (1RS,3RS,4SR)-1,4-dimethyl-1-methoxy-3-[3-(1-methyl-2-oxo-1,2-dihydroquinolin-6-ylmethoxy)phenyl]cyclohexane as an oil in 41% yield.

NMR Spectrum 0.66 (d, 3H), 1.28 (s, 3H), 1.55–1.87 (m, 5H), 1.9–2.1 (m, 2H), 2.91 (m, 1H), 3.30 (s, 3H), 3.74 (s, 3H), 5.11 (s, 2H), 6.75–6.82 (m, 4H), 7.20–7.24 (m, 1H), 7.38–7.40 (d, 1H), 7.63–7.69 (m, 3H).

EXAMPLE 11

A solution of (3RS,4SR)-4-methyl-3-[3-(1-methyl-2-oxo-1,2-dihydroquinolin-6-ylmethoxy)phenyl]cyclohexanone (0.075 g) in carbon tetrachloride (0.7 ml) was added to a mixture of montmorrillonite clay (0.008 g), triethyl orthoformate (0.066 ml) and ethylene glycol (0.012 ml). The mixture was stirred and heated to 65° C. for 24 hours. The mixture was cooled to ambient temperature and filtered. The filtrate was partitioned between diethyl ether and a saturated aqueous sodium bicarbonate solution. The organic phase was washed with brine, dried (MgSO₄) and evaporated. The residue was purified by column chromatography using a 1:9 mixture of petroleum ether and ethyl acetate as eluent.

There was thus obtained (3RS,4SR)-4-methyl-3-[3-(1-methyl-2-oxo-1,2-dihydroquinolin-6-ylmethoxy)phenyl]cyclohexanone ethylene acetal (0.058 g, 69%), m.p. 133°–135° C.

NMR Spectrum 0.67 (d, 3H), 1.43–2.07 (m, 7H), 3.13–3.19 (m, 1H), 3.77 (s, 3H), 3.92–3.99 (m, 4H), 5.11 (s, 2H), 6.72–6.82 (m, 4H), 7.2–7.24 (m, 1H), 7.38 (d, 1H), 7.63–7.69 (m, 3H).

EXAMPLE 12

A mixture of (3RS,4SR)-4-methyl-3-[3-(1-methyl-2-oxo-1,2-dihydroquinolin-6-ylmethoxy)phenyl]cyclohexanone (0.116 g), hydroxylamine hydrochloride (0.034 g) and pyridine (1.2 ml) was stirred and heated to 80° C. for 90 minutes. The mixture was poured into water, acidified to pH4 by the addition of dilute aqueous hydrochloric acid and extracted with ethyl acetate. The organic phase was washed with water and with brine, dried (MgSO₄) and evaporated. The residue was purified by column chromatography using a 7:3 mixture of ethyl acetate and methylene chloride as eluent. There was thus obtained (3RS,4SR)-4-methyl-3-[3-(1-methyl-2-oxo-1,2-dihydroquinolin-6-ylmethoxy)phenyl]cyclohexanone oxime (0.051 g, 42%), m.p. 81°–87° C.

NMR Spectrum 0.68 (d, 3H), 1.5–1.8 (m, 3H), 2.05–2.65 (m, 4H), 2.9–3.0 (m, 1H), 3.66 (s, 3H), 5.04 (s, 2H), 6.6–6.7 (d, 1H), 6.7–6.8 (m, 3H), 7.1–7.2 (m, 1H), 7.3–7.4 (d, 1H), 7.5–7.7 (m, 3H).

EXAMPLE 13

The procedure described in Example 12 was repeated except that O-methylhydroxylamine was used in place of hydroxylamine hydrochloride. There was thus obtained (3RS,4SR)-4-methyl-3-[3-(1-methyl-2-oxo-1,2-dihydroquinolin-6-ylmethoxy)phenyl]cyclohexanone oxime O-methyl ether in 82% yield as a foam.

NMR Spectrum 0.75 (d, 3H), 1.5–1.9 (m, 3H), 2.1–2.65 (m, 4H), 2.9–3.1 (m, 1H), 3.74 (s, 3H), 3.8–3.9 (2 s's, 3H), 5.11 (s, 2H), 6.65–6.9 (m, 4H), 7.15–7.3 (m, 1H), 7.35–7.45 (d, 1H), 7.55–7.75 (m, 3H).

EXAMPLE 14

Trimethyl orthoformate (1.2 ml) was added to montmorillonite clay (0.8 g) and the mixture was shaken for 5 minutes and filtered. The solid so obtained was added to a mixture of (3RS,4SR)-4-methyl-3-[3-(1-methyl-2-oxo-1,2-dihydroquinolin-6-ylmethoxy)phenyl]cyclopentanone (0.141 g), chloroform (0.5 ml) and carbon tetrachloride (5 ml). The mixture was stirred and heated to 45° C. for 3 hours. The mixture was cooled to ambient temperature and basified by the addition of sodium bicarbonate. The mixture was diluted with ethyl acetate and stirred for 5 minutes. The mixture was filtered and evaporated. There was thus obtained (3RS,4SR}-1,1-dimethoxy-4-methyl-3-[3-(1-methyl-2-oxo-1,2-dihydroquinolin-6-ylmethoxy)phenyl]cyclopentane as an oil (0.07 g, 44%).

NMR Spectrum 0.63 (d, 3H), 1.65 (m, 1H), 2.13 (m, 2H), 2.20 (m, 1H), 2.41 (m, 1H), 3.23 (s, 3H), 3.28 (s, 3H), 3.35 (m, 1H), 3.74 (s, 5.12 (s, 2H), 6.72–6.88 (m, 4H), 7.23 (m, 1H), 7.39 (m, 1H), 7.66 (m, 3H).

The (3RS,4SR)-4-methyl-3-[3-(1-methyl-2-oxo-1,2-dihydroquinolin-6-ylmethoxy)phenyl]cyclopentanone used as a starting material was obtained as follows:

A solution of 3-chloro-2-methylpropene (4.35 g) in THF (10 ml) was added dropwise to a mixture of 3-benzyloxyphenyl ethyl ketone (7.68 g), sodium hydride (60% w/w dispersion in mineral oil, 2.4 g, from which the oil had been removed by washing with petroleum ether) and THF (70 ml). The mixture was stirred and heated to reflux for 16 hours. The mixture was cooled to ambient temperature and acidified to pH6 by the addition of dilute aqueous hydrochloric acid. The mixture was extracted with diethyl ether. The organic phase was washed with water and with brine, dried (MgSO4) and evaporated. The residue was purified by column chromatography using a 3:2 mixture of methylene chloride and petroleum ether as eluent. There was thus obtained 3-benzyloxyphenyl 2-methylpent-1-en-4-yl ketone as an oil (6.1 g, 51%).

Sodium metaperiodate (8.56 g) and ruthenium(III) chloride trihydrate (0.052 g) were added in turn to a vigorously stirred mixture of a portion (2.94 g) of the ketone so obtained, carbon tetrachloride (20 ml), acetonitrile (20 ml) and water (30 ml). The mixture was stirred at ambient temperature for 1 hour. Methanol (3 ml) was added and the mixture was stirred for 10 minutes. The mixture was partitioned between methylene chloride and water. The organic phase was dried (MgSO4) and evaporated. The residue was purified by column chromatography using a 19:1 mixture of methylene chloride and diethyl ether as eluent. There was thus obtained 3-benzyloxyphenyl 2-oxopent-4-yl ketone as an oil (1.55 g, 52%).

Potassium tert-butoxide (0.112 g) was added to a solution of a portion (1.2 g) of the ketone so obtained in tert-butanol (15 ml) and the mixture was stirred at ambient temperature for 30 minutes. The mixture was partitioned between diethyl ether and a saturated aqueous ammonium chloride solution. The organic phase was washed with dilute aqueous hydrochloric acid, dried (MgSO4) and evaporated. The residue was purified by column chromatography using a 19:1 mixture of methylene chloride and diethyl ether as eluent. There was thus obtained 3-(3-benzyloxyphenyl)-4-methylcyclopent-2-en-1-one as an oil (0.81 g, 80%).

NMR Spectrum 1.21 (d, 3H), 2.2 (d, 1H), 2.83 (m, 1H), 3.48 (m, 1H), 5.11 (s, 2H), 6.38 (s, 1H), 7.05–7.46 (m, 9H).

After repetition of the above-mentioned step, a mixture of the cyclopentenone so obtained (1.28 g), 10% palladium-on-charcoal catalyst (0.3 g), ethyl acetate (10 ml) and methanol (25 ml) was stirred under 5 atmospheres pressure of hydrogen for 45 minutes. The mixture was filtered and evaporated. The residue was purified by column chromatography using a 19:1 mixture of methylene chloride and diethyl ether as eluent. There was thus obtained (3RS,4SR)-3-(3-benzyloxyphenyl)-4-methylcyclopentanone as an oil (0.48 g, 37%).

NMR Spectrum 0.72 (d, 3H), 2.13 (m, 1H), 2.48 (m, 1H), 2.49–2.67 2H), 2.70 (m, 1H), 3.56 (m, 1H), 5.07 (s, 2H), 6.74 (m, 2H), 6.87 (m, 1H), 7.22–7.44 (m, 6H).

The solid, obtained when trimethyl orthoformate (3 ml) was added to montmorillonite clay (0.45 g) and the mixture was stirred for 5 minutes and filtered, was added to a solution of (3RS,4SR)-3-(3-benzyloxyphenyl)-4-methylcyclopentanone (0.42 g) in carbon tetrachloride (6 ml). The mixture was stirred at ambient temperature for 1 hour. The mixture was basified by the addition of sodium bicarbonate. Diethyl ether was added and the mixture was filtered. The filtrate was washed with brine, dried (MgSO4) and evaporated. There was thus obtained (3RS,4SR)-3-(3-benzyloxyphenyl)-1,1-dimethoxy-4-methylcyclopentanone as an oil (0.4 g, 82%).

A mixture of the product so obtained, 10% palladium-on-charcoal catalyst (0.1 g), ethyl acetate (5 ml) and methanol (10 ml) was stirred under 5 atmospheres pressure of hydrogen for 3.5 hours. The mixture was filtered and evaporated. There was thus obtained (3RS,4SR)-3-(3-hydroxyphenyl)-4-methylcyclopentanone as an oil (0.25 g).

Using an analogous procedure to that described in Example 5, the cyclopentanone so obtained was reacted with 6-bromomethyl-1-methyl-1,2-dihydroquinolin-2-one to give (3RS,4SR)-4-methyl-3-[3-(1-methyl-2-oxo-1,2-dihydroquinolin-6-ylmethoxy)phenyl]cyclopentanone as a foam in 60% yield.

NMR Spectrum 0.73 (d, 3H), 2.12 (m, 1H), 2.37–2.75 (m, 4H), 3.59 (m, 1H), 3.74 (s, 3H), 5.13 (s, 2H), 6.77 (m, 3H), 6.89 (m, 1H), 7.28 (m, 1H), 7.41 (m, 1H), 7.65 (m, 3H).

EXAMPLE 15

The following illustrate representative pharmaceutical dosage forms containing the compound of formula I, or a pharmaceutically-acceptable salt thereof (hereafter compound X), for therapeutic or prophylactic use in humans:

| (a) Tablet I | mg/tablet |
|---|---|
| Compound X | 100 |
| Lactose Ph.Eur | 182.75 |
| Croscarmellose sodium | 12.0 |
| Maize starch paste (5% w/v paste) | 2.25 |
| Magnesium stearate | 3.0 |
| (b) Tablet II | |
| Compound X | 50 |
| Lactose Ph.Eur | 223.75 |
| Croscarmellose sodium | 6.0 |
| Maize starch | 15.0 |
| Polyvinylpyrrolidone (5% w/v paste) | 2.25 |
| Magnesium stearate | 3.0 |
| (c) Tablet III | |
| Compound X | 1.0 |
| Lactose Ph.Eur | 93.25 |
| Croscarmellose sodium | 4.0 |
| Maize starch paste (5% w/v paste) | 0.75 |
| Magnesium stearate | 1.0 |
| (d) Capsule | mg/capsule |
| Compound X | 10 |
| Lactose Ph.Eur | 488.5 |
| Magnesium stearate | 1.5 |
| (e) Injection I | (50 mg/ml) |
| Compound X | 5.0% w/v |
| 1M Sodium hydroxide solution | 15.0% v/v |
| 0.1M Hydrochloric acid (to adjust pH to 7.6) | |
| Polyethylene glycol 400 | 4.5% w/v |
| Water for injection to 100% | |
| (f) Injection II | (10 mg/ml) |
| Compound X | 1.0% w/v |
| Sodium phosphate BP | 3.6% w/v |
| 0.1M Sodium hydroxide solution | 15.0% v/v |
| Water for injection to 100% | |
| (g) Injection III | (1 mg/ml, buffered to pH 6) |
| Compound X | 0.1% w/v |
| Sodium phosphate BP | 2.26% w/v |
| Citric acid | 0.38% w/v |
| Polyethylene glycol 400 | 3.5% w/v |
| Water for injection to 100% | |
| (h) Aerosol I | mg/ml |
| Compound X | 10.0 |
| Sorbitan trioleate | 13.5 |
| Trichlorofluoromethane | 910.0 |
| Dichlorodifluoromethane | 490.0 |
| (i) Aerosol II | |
| Compound X | 0.2 |
| Sorbitan trioleate | 0.27 |

-continued

| | | |
|---|---|---|
| | Trichlorofluoromethane | 70.0 |
| | Dichlorodifluoromethane | 280.0 |
| | Dichlorotetrafluoroethane | 1094.0 |
| (j) | Aerosol III | |
| | Compound X | 2.5 |
| | Sorbitan trioleate | 3.38 |
| | Trichlorofluoromethane | 67.5 |
| | Dichlorodifluoromethane | 1086.0 |
| | Dichlorotetrafluoroethane | 191.6 |
| (k) | Aerosol IV | |
| | Compound X | 2.5 |
| | Soya lecithin | 2.7 |
| | Trichlorofluoromethane | 67.5 |
| | Dichlorodifluoromethane | 1086.0 |
| | Dichlorotetrafluoroethane | 191.6 |

Note

The above formulations may be obtained by conventional procedures well known in the pharmaceutical art. The tablets (a)–(c) may be enteric coated by conventional means, for example to provide a coating of cellulose acetate phthalate. The aerosol formulations (h)–(k) may be used in conjunction with standard, metered dose aerosol dispensers, and the suspending agents sorbitan trioleate and soya lecithin may be replaced by an alternative suspending agent such as sorbitan monooleate, sorbitan sesquioleate, polysorbate 80, polyglycerol oleate or oleic acid.

CHEMICAL FORMULAE

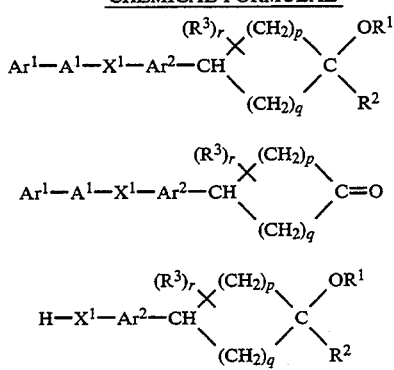

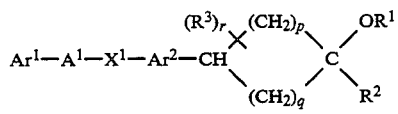

We claim:

1. A cycloalkane derivative of the formula I

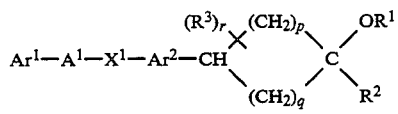

wherein

Ar$^1$ is quinolyl, or a hydrogenated derivative thereof and Ar$^1$ may optionally bear up to four substituents selected from halogeno, hydroxy, cyano, oxo, thioxo, (1–4C)alkyl, (1–4C)alkoxy, fluoro-(1–4C)alkyl, phenyl, benzoyl and phenyl-(1–4C)alkyl and wherein any phenyl, benzoyl or phenyl-(1–4C)alkyl substituent may optionally bear one or two substituents selected from halogeno, (1–4C)alkyl and (1–4C)alkoxy;

A$^1$ is a direct link to X$^1$ or is (1–3C)alkylene;

X$^1$ is oxy, thio, sulphinyl or sulphonyl;

Ar$^2$ is phenylene, pyridylene, pyrimidinylene, thiophenediyl, furandiyl, thiazolediyl or oxazolediyl which may optionally bear one or two substituents selected from halogeno, hydroxy, amino, nitro, cyano, carbamoyl, trifluoromethyl, (1–4C)alkyl and (1–4C)alkoxy;

p is 1 to 4;

q is 0 to 2;

R$^1$ is hydrogen, (1–4C)alkyl, (2–4C)alkenyl or (3–4C)alkynyl;

R$^2$ is hydrogen, hydroxy, (1–4C)alkyl, (1–4C)alkoxy, (2–4C)alkenyloxy or (3–4C)alkynyloxy;

or the OR$^1$ and R$^2$ groups together form a (1–4C)alkylenedioxy, oxo, thioxo, imino, hydroxyimino or (1–4C)alkoxyimino group;

r is 0 to 3; and

R$^3$ is halogeno, trifluoromethyl or (1–4C)alkyl;

or a pharmaceutically-acceptable salt thereof.

2. A cycloalkane derivative of the formula I as claimed in claim 1 wherein

Ar$^1$ is 2-oxo-1,2-dihydroquinolinyl or 2-oxo-1,2,3,4-tetrahydroquinolinyl which may optionally bear one, two or three substituents selected from fluoro, chloro, methyl, ethyl, 2-fluoroethyl, phenyl and benzyl;

A$^1$ is a direct link to X$^1$, or is methylene;

X$^1$ is oxy, thio, sulphinyl or sulphonyl;

Ar$^2$ is 1,3-phenylene which may optionally bear one substituent selected from fluoro, chloro and trifluoromethyl;

p is 2 or 3;

q is 1;

R$^1$ is hydrogen, methyl, ethyl or propyl;

R$^2$ is hydrogen, hydroxy, methyl, ethyl, propyl, methoxy, ethoxy or propoxy;

or the OR$^1$ and R$^2$ groups together form an ethylenedioxy.

3. A cycloalkane derivative of the formula I as claimed in claim 1 wherein

Ar$^1$ is 1-methyl-2-oxo-1,2-dihydroquinolin-6-yl;

A$^1$ is methylene and X$^1$ is oxy, or A$^1$ is a direct link to X$^1$ and X$^1$ is thio;

Ar$^2$ is 1,3-phenylene or 5-fluoro-1,3-phenylene;

p is 2 or 3;

q is 1;

R$^1$ is methyl or ethyl;

R$^2$ is hydrogen, methoxy or ethoxy;

r is 1 or 2, R$^3$ is independently methyl or ethyl and at least one R$^3$ group is located on the carbon atom within the —(CH$_2$)$_p$— group which is attached to the carbon atom which bears the Ar$^2$ group;

or a pharmaceutically-acceptable salt thereof.

4. A cycloalkane derivative of the formula I as claimed in claim 1 wherein Ar$^1$ is 1-methyl-2-oxo-1,2-dihydroquinolin-6-yl;

A$^1$ is methylene and X$^1$ is oxy;

Ar$^2$ is 1,3-phenylene or 5-fluoro-1,3-phenylene;

p is 3;

q is 1;

R$^1$ is methyl or ethyl;

R$^2$ is methoxy or ethoxy;

r is 1 and R$^3$ is methyl which is located on the carbon atom within the —(CH$_2$)$_p$— group which is attached to the carbon atom which bears the Ar$^2$ group such that the R$^3$ and Ar$^2$ groups are in a cis-relationship;

or a pharmaceutically-acceptable salt thereof.

5. The cycloalkane derivative of the formula I, or a pharmaceutically-acceptable salt thereof, as claimed in claim 1 selected from (3RS,4SR)-1,1-dimethoxy-4-methyl-3-[3-(1-methyl-2-oxo-1,2-dihydroquinolin-6-ylmethoxy)phenyl]cyclohexane or the (3RS,4RS)-isomer thereof, and
1-methoxy-4-methyl-3-[3-(1-methyl-2-oxo-1,2-dihydroquinolin-6-ylmethoxy)phenyl]cyclohexane.

6. The cycloalkane derivative of the formula I, or a pharmaceutically-acceptable salt thereof, as claimed in claim 1 selected from
1,1-dimethoxy-3-[3-(1-methyl-2-oxo-1,2-dihydroquinolin-6-ylmethoxy)phenyl]cyclohexane,
(1SR,3RS,4SR)-1-methoxy-4-methyl-3-[3-(1-methyl-2-oxo-1,2-dihydroquinolin-6-ylmethoxy)phenyl]cyclohexane or the (1RS,3RS,4SR)-isomer thereof,
(1SR,3RS,4SR)-1,4-dimethyl-1-hydroxy-3-[3-(1-methyl-2-oxo-1,2-dihydroquinolin-6-ylmethoxy)phenyl]cyclohexane,
(1SR,3RS,4SR)-1,4-dimethyl-1-methoxy-3-[3-(1-methyl-2-oxo-1,2-dihydroquinolin-6-ylmethoxy)phenyl]cyclohexane,
(3RS,4SR)-4-methyl-3-[3-(1-methyl-2-oxo-1,2-dihydroquinolin-6-ylmethoxy)phenyl]cyclohexanone ethylene acetal and
(3RS,4SR)-1,1-dimethoxy-4-methyl-3-[3-(1-methyl-2-oxo-1,2-dihydroquinolin-6-ylmethoxy)phenyl]cyclopentane.

7. A pharmaceutical composition which comprises a cycloalkane derivative of the formula I, or a pharmaceutically-acceptable salt thereof, as claimed in any one of claims 1 to 6 in association with a pharmaceutically-acceptable diluent or carrier.

8. A method of treating a disease or medical condition mediated alone or in part by one or more leukotrienes which comprises administering to a warm-blooded animal requiring such treatment an effective amount of a cycloalkane derivative of the formula I, or a pharmaceutically-acceptable salt thereof, as claimed in any one of claims 1 to 6.

* * * * *